(12) United States Patent
Johnson

(10) Patent No.: US 10,143,670 B2
(45) Date of Patent: Dec. 4, 2018

(54) ANTIMICROBIALS AND METHODS OF USE THEREOF

(71) Applicant: Lanny Leo Johnson, Frankfort, MI (US)

(72) Inventor: Lanny Leo Johnson, Frankfort, MI (US)

( * ) Notice: Subject to any disclaimer, the term of this patent is extended or adjusted under 35 U.S.C. 154(b) by 0 days.

(21) Appl. No.: 15/787,343

(22) Filed: Oct. 18, 2017

(65) Prior Publication Data

US 2018/0071235 A1    Mar. 15, 2018

Related U.S. Application Data

(60) Division of application No. 15/484,827, filed on Apr. 11, 2017, now Pat. No. 10,016,380, which is a continuation-in-part of application No. 15/189,510, filed on Jun. 22, 2016, now Pat. No. 9,925,152, which is a division of application No. 14/264,553, filed on Apr. 29, 2014, now Pat. No. 9,498,413.

(60) Provisional application No. 61/818,275, filed on May 1, 2013.

(51) Int. Cl.

| | |
|---|---|
| *A61K 31/11* | (2006.01) |
| *A61K 31/192* | (2006.01) |
| *A61K 9/00* | (2006.01) |
| *A61K 9/08* | (2006.01) |
| *A61K 9/127* | (2006.01) |
| *A61L 15/44* | (2006.01) |
| *A61L 2/18* | (2006.01) |
| *A23L 3/3481* | (2006.01) |
| *A23L 3/349* | (2006.01) |
| *A23L 3/3508* | (2006.01) |
| *A01N 35/04* | (2006.01) |
| *A23L 3/3544* | (2006.01) |
| *A01N 37/40* | (2006.01) |
| *A01N 43/16* | (2006.01) |
| *A23B 7/154* | (2006.01) |
| *A61K 8/34* | (2006.01) |
| *A61K 8/368* | (2006.01) |
| *A61K 8/60* | (2006.01) |
| *A61Q 17/00* | (2006.01) |
| *A61Q 19/08* | (2006.01) |
| *A61K 45/06* | (2006.01) |
| *A61K 8/14* | (2006.01) |
| *A61K 31/352* | (2006.01) |
| *A61K 31/7048* | (2006.01) |
| *A01N 31/02* | (2006.01) |

(52) U.S. Cl.

CPC ............ *A61K 31/192* (2013.01); *A01N 31/02* (2013.01); *A01N 35/04* (2013.01); *A01N 37/40* (2013.01); *A01N 43/16* (2013.01); *A23B 7/154* (2013.01); *A23L 3/349* (2013.01); *A23L 3/3481* (2013.01); *A23L 3/3508* (2013.01); *A23L 3/3544* (2013.01); *A61K 8/14* (2013.01); *A61K 8/347* (2013.01); *A61K 8/368* (2013.01); *A61K 8/602* (2013.01); *A61K 9/0014* (2013.01); *A61K 9/08* (2013.01); *A61K 9/127* (2013.01); *A61K 31/11* (2013.01); *A61K 31/352* (2013.01); *A61K 31/7048* (2013.01); *A61K 45/06* (2013.01); *A61L 2/18* (2013.01); *A61L 15/44* (2013.01); *A61Q 17/005* (2013.01); *A61Q 19/08* (2013.01); *A23V 2002/00* (2013.01); *A61L 2300/404* (2013.01); *Y02A 50/473* (2018.01); *Y02A 50/478* (2018.01)

(58) Field of Classification Search

None
See application file for complete search history.

(56) References Cited

U.S. PATENT DOCUMENTS

| | | | | |
|---|---|---|---|---|
| 4,880,416 | A | * | 11/1989 | Horiuchi ............ A61K 9/7053 424/427 |
| 4,997,850 | A | | 3/1991 | Kimura et al. |
| 2003/0069317 | A1 | | 4/2003 | Seitz, Jr. et al. |
| 2005/0100622 | A1 | | 5/2005 | Nair et al. |
| 2006/0293258 | A1 | | 12/2006 | Rohdewald |
| 2008/0033329 | A1 | * | 2/2008 | Downs ............... A61F 13/0273 602/41 |
| 2008/0234618 | A1 | * | 9/2008 | Baldock ........... A61F 13/00063 602/48 |
| 2009/0304885 | A1 | | 12/2009 | Perry |

(Continued)

FOREIGN PATENT DOCUMENTS

| | | |
|---|---|---|
| CN | 102048481 A | 5/2011 |
| CN | 105647674 A | 6/2016 |

(Continued)

OTHER PUBLICATIONS

Kakkar S, A review on protocatechuic acid and its pharmacological potential, ISRN Pharmacology, vol. 2014, article ID 952943, 9 pages, Mar. 26, 2014 (Year: 2014).*

(Continued)

*Primary Examiner* — Celeste A Roney
(74) *Attorney, Agent, or Firm* — Brinks Gilson & Lione; Ryan L. Marshall; Bryan T. Richardson

(57) ABSTRACT

This disclosure provides generally for antimicrobial compositions and methods of use comprising an anthocyanin, an anthocyanidin or metabolites thereof. Methods for promoting healing of a wound using these compositions are also disclosed. These compositions have broad spectrum antimicrobial activity and are safe for human and animal uses. Further, these compositions are safe for medical uses and industrial uses as antiseptic preparations to reduce or prevent microbial growth, including killing bacterial biofilms.

22 Claims, 27 Drawing Sheets

(56) References Cited

U.S. PATENT DOCUMENTS

| | | | |
|---|---|---|---|
| 2010/0004469 A1 | 1/2010 | Shigehara et al. | |
| 2010/0029574 A1 | 2/2010 | Marini | |
| 2010/0204204 A1* | 8/2010 | Zaworotko | A61K 31/20 514/212.03 |
| 2011/0104243 A1* | 5/2011 | Singhal | A61L 15/46 424/446 |
| 2011/0268825 A1 | 11/2011 | Burgos et al. | |
| 2013/0231302 A1 | 9/2013 | Raad et al. | |
| 2014/0328902 A1 | 11/2014 | Johnson | |

FOREIGN PATENT DOCUMENTS

| | | |
|---|---|---|
| JP | 2010-184900 A | 8/2010 |
| WO | WO 2008/126980 A1 | 10/2008 |
| WO | WO 2009/003899 A1 | 1/2009 |

OTHER PUBLICATIONS

Chao, Che-Yi, et al., "Antibacterial Effects of Roselle Calyx Extracts and Protocatechuic Acid in Ground Beef and Apple Juice," *Foodborne Pathogens and Disease*, vol. 00, No. 00, pp. 1-7 (2008).

El Maghraby, G., "Skin delivery of 5-fluorouracil from ultradeformable and standard liposomes in vitro," *Journal of Pharmacy and Pharmacology*, 53:1069-1077 (2001).

Friedman, et al., "Antibacterial Activities of Phenolic Benzaldehydes and Benzoic Acids against Camylobacter jejuni, *Escherichia coli*, Listeria monocytogenes, and *Salmonella enterica*," *Journal of Food Protection*, 66(10):1811-1821 (2003).

Gu, Zheng-yi, "Effect of pomegranate peel polyphenol gel on cutaneous wound healing in alloxan-induced diabetic rats," *Chinese Medical Journal*, 126(9):1700-1706 (2013).

International Search Report from corresponding International Application No. PCT/US2014/035881, 4 pages, dated Nov. 3, 2014.

Jayaraman, P., et al., "Activity and interactions of antibiotic and phytochemical combinations against *Pseudomonas aeruginosa* in vitro," *International Journal of Biological Sciences*, 6(6):556-568 (2010).

Kakkar, S., et al., "A Review on Protocatechuic Acid and Its Pharmacological Potential," *Hindawi Publishing Company, ISRN Pharmacology*, vol. 2014, 9 pages.

Liu, Keh-sen, et al., "In vitro Antibacterial Activity of Roselle Calyx and Protocatechuic Acid," *Phytotherapy Research*, 19:942-945 (2005).

Nizamutdinova, I.T., et al., "Anthocyanins from black soybean seed coats stimulate wound healing in fibroblasts and keratinocytes and prevent inflammation in endothelial cells," *Food and Chemical Toxicology*, 47:2806-2812 (2009).

Proestos, C., et al., "Analysis of flavonoids and phenolic acids in Greek aromatic plants: Investigation of their antioxidant capacity and antimicrobial activity," *Food Chemistry*, 95:664-671 (2006).

Semaming, Yoswaris, et al., "Pharmacological Properties of Protocatechuic Acid and Its Potential Roles as Complementary Medicine," *Evidence-Based Complementary and Alternative Medicine*, vol. 2015, 11 pages.

Sivamani, R.K., et al., "Phytochemicals and Naturally Derived Substances for Wound Healing," *Advances in Wound Care*, 1(5):213-217 (Oct. 2012).

Zillich, O.V., et al., "Release and in vitro skin permeation of polyphenols from cosmetic emulsions," *International Journal of Cosmetic Science*, 35(5):491-501 (Oct. 2013).

Alves, M.J., et al., "Antimicrobial activity of phenolic compounds identified in wild mushrooms, SAR analysis and docking studies," Journal of Applied Microbiology, ISSN 1364-5072, 12 pages (2013).

Almeida, Ana Amelia P., et al., "Antibacterial Activity of Coffee Extracts and Selected Coffee Chemical Compounds against Enterobacteria," *J. Agric. Food Chem.*, 54:8738-8743 (2006).

De Vita, Daniela, et al., "Activity of caffeic acid derivatives against Candida albicansbiofilm," *Bioorganic & Medicinal Chemistry Letters*, 24(6):1502-1505 (2014).

Donlan, R M, "Biofilms: Microbial life on surfaces," *Emerging Infectious Diseases*, EID, Atlanta, GA, US, 8(9): 881-890 (2002).

Gutierrez, Sergio, et al., "The Usefulness of Non-Toxic Plant Metabolites in the Control of Bacterial Proliferation", *Probiotics and Antimicrobial Proteins*, New York, NY; Heidelberg: Springer, New York, Ny ; Heidelberg : Springer, 9(3):323-333 (2017).

Moran, A., et al., "Non-toxic plant metabolites regulate *Staphylococcus* viability and biofilm formation: a natural therapeutic strategy useful in the treatment and prevention of skin infections," *Biofouling: The Journal of Bioadhesion and Biofilm Research*, 30(10):1175-1182 (2014).

Uberos, J., et al., "Phenolic acid content and antiadherence activity in the urine of patients treated with cranberry syrup (*Vaccinium macrocarpon*) vs. trimethoprim for recurrent urinary tract infection," *Journal of Functional Foods*, 18:608-616 (2015).

\* cited by examiner

Minimum, maximum and optimum pH for growth of certain procaryotes.

| Organism | Minimum pH | Optimum pH | Maximum pH |
|---|---|---|---|
| Thiobacillus thiooxidans | 0.5 | 2.0-2.8 | 4.0-6.0 |
| Sulfolobus acidocaldarius | 1.0 | 2.0-3.0 | 5.0 |
| Bacillus acidocaldarius | 2.0 | 4.0 | 6.0 |
| Zymomonas lindneri | 3.5 | 5.5-6.0 | 7.5 |
| Lactobacillus acidophilus | 4.0-4.6 | 5.8-6.6 | 6.8 |
| Staphylococcus aureus | 4.2 | 7.0-7.5 | 9.3 |
| Escherichia coli | 4.4 | 6.0-7.0 | 9.0 |
| Clostridium sporogenes | 5.0-5.8 | 6.0-7.6 | 8.5-9.0 |
| Erwinia caratovora | 5.6 | 7.1 | 9.3 |
| Pseudomonas aeruginosa | 5.6 | 6.6-7.0 | 8.0 |
| Thiobacillus novellus | 5.7 | 7.0 | 9.0 |
| Streptococcus pneumoniae | 6.5 | 7.8 | 8.3 |
| Nitrobacter sp | 6.6 | 7.6-8.6 | 10.0 |

FIG. 1

| Organism | C. difficile 9689 | P.acnes 6919 | C.Prefringens 13124 | L. casei 393 | C.albicans | E. coli 8739 | |
|---|---|---|---|---|---|---|---|
| Amoxicillin | I/CZ/27 mm | I/CZ/36 mm | I/CZ/27 mm | I/CZ/27mm | NI/NZ | I/CZ/15mm | |
| Delphinidin | NI/NZ | I/NZ | I/CZ/8mm | I/NZ | NI/NZ | NI/NZ | |
| Pelargonidin | NI/NZ | I/CZ/1mm | I/CZ/9mm | NI/NZ | NI/NZ | NI/NZ | |
| Cyanidin Cl | I/NZ | NI/NZ | I/CZ/6mm | NI/NZ | NI/NZ | NI/NZ | |
| 28% C-3-G | NI/NZ | I/CZ/23 mm | NI/NZ | NI/NZ | N/i/NZ | I/NZ | |
| PCA | I/CZ/1mm | I/CZ/22 mm | I/CZ/5.5mm | I/CZ/5mm | I/CZ/0.5mm | I/CZ/4.5mm | |
| 246THBA | NI/NZ | NI/NZ | NI/NZ | I/NZ | I/CZ 4 mm | I/CZ/ 6 mm | |
| Organism | | E. coli 43895 | S.aureus 6538 | S.aureus 33591 | S. mutans 25175 | S.pyogenes 19615 | P.aeruginosa 9027 | K. pneumonia 4352 |
| Amoxicillin | | | I/CZ/13mm | I/CZ/24 mm | I/CZ/9mm | I/CZ/34mm | | NI/NZ |
| Delphinidin | | | NI/NZ | I/CZ/10mm | I/CZ/7mm | I/NZ | | NI/NZ |
| Pelargonidin | | | NI/NZ | I/CZ/3mm | I/CZ/4mm | NI/NZ | | NI/NZ |
| Cyanidin Cl | | | NI/NZ | I/CZ/1mm | I/CZ/3mm | NI/NZ | | NI/NZ |
| 28% C-3-G | | | I/CZ/0.3mm | I/NZ | I/CZ/4mm | I/NZ | I/NZ | I/CZ/1mm |
| PCA | | I/CZ/9mm | I/CZ/8mm | I/CZ/9mm | I/CZ/1mm | I/CZ/2.5mm | I/CZ/10mm | I/CZ/1mm |
| 246THBA | | I/CZ/3mm | I/CZ/13mm | I/C/14mmZ | I/CZ/2mm | I/CZ 3 mm | I/CZ/ 3 mm | I/CZ/6mm |

NI = No inhibition of growth
NZ= No zone
I= Inhibition
CZ= Clear zone

FIG. 6

2,4,6 Trihydroxybenzaldehyde In vitro Testing:

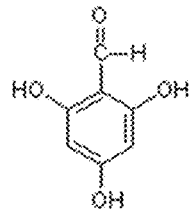

Interpretation of Results:

NZ / C = No zone was seen, however there was clearing of growth directly underneath the sample.

NZ / NC = No zone / No clearing of growth underneath the sample.

CZ = Clear zone

| SAMPLE ID | ORGANISM | ZONE OF INHIBITION |
|---|---|---|
| 1 | Aspergillus fumigatus   ATCC 1022 | NI /NZ |
|   | Clostridium difficile   ATCC 9689 | NI /NZ |
|   | Clostridium perfringens   ATCC 13124 | NI /NZ |
|   | Penicillium chrysogenum   ATCC 10134 | NI /NZ |
|   | Propionobacterium acnes   ATCC 6919 | NI /NZ |
|   | Streptococcus mutans   ATCC 25175 | I / CZ / 2 mm |
|   | Streptococcus pyogenes   ATCC 19615 | I / CZ / 3 mm |
|   | Trichophyton rubrum   ATCC 38484 | NI /NZ |

| SAMPLE ID | ORGANISM | ZONE OF INHIBITION |
|---|---|---|
| 1 | Candida albicans   ATCC 10231 | I / NZ |
|   | Lactobacillus casei   ATCC 393 | I / CZ / 4 mm |

FIG. 7

Zero Time: Control Group 1 (untreated and uninfected)

H&E X100

H&E X200

Two hours: Control Group 1 (untreated and uninfected)

H&E X100

H&E X200

48 hours: Control Group 1 (untreated and uninfected)

H&E X100

H&E X 200

2 hours: Control Group 2 (untreated and infected)

H&E X100 (2A)

H&E X200 (2A)

48 hours: Control Group 2 (untreated and infected)

H&E X100

H&E X200

48 hours: Experimental Group 1 (PCA 25 mM)

H&E X100 (9c)

H&E X200 (9c)

48 hours: Experimental Group (PCA 50 mM)

H&E X100 (5b)

H&E X200 (5b)

48 hours: Experimental Group (C3G 100 mM)

H&E X100 (19c)

H&E X200 (19c)

48 hours: Experimental Group (C3G 200 mM)

FIG. 32

Pseudomonas Results

10% Concentration not as Effective

|            | CFU / Coupon          | Log Density |
|------------|-----------------------|-------------|
| Cloth 2%   | $1.2 \times 10^{10}$  | 10.5        |
| Cloth 2%   | $1.6 \times 10^{10}$  | 10.6        |
| Cloth 10%  | $1.4 \times 10^{10}$  | 10.6        |
| Cloth 10%  | $8.9 \times 10^{9}$   | 10.4        |
| 3 ply 10%  | $3.9 \times 10^{9}$   | 10.0        |
| 3 ply 10%  | $4.5 \times 10^{9}$   | 10.1        |
| 5 ply 10%  | $3.6 \times 10^{9}$   | 10.0        |
| 5 ply 10%  | $6.9 \times 10^{8}$   | 9.3         |

- CFU: Colony Forming Units is estimation of # viable bacteria
- Coupon is the article of cloth or stainless steel mesh
- Log Density is calculation of biofilm present

FIG. 33

Pseudomonas Results
20% Concentration was Very Effective

| | (CFU / Coupon) | Log Density |
|---|---|---|
| Cloth | $1.3 \times 10^2$ | 2.5 |
| Cloth | $1.0 \times 10^1$ | 1.4 |
| 3 ply metal | $< 1.0 \times 10^1$ | $< 1.4$ |
| 3 ply metal | $< 1.0 \times 10^1$ | $< 1.4$ |
| 5 ply metal | $< 1.0 \times 10^1$ | $< 1.4$ |
| 5 ply metal | $< 1.0 \times 10^1$ | $< 1.4$ |
| Glass slide | $7.1 \times 10^7$ | 8.3 |
| Glass slide | $7.5 \times 10^6$ | 7.3 |
| Crystals 3 ply | $< 1.0 \times 10^1$ | $< 1.4$ |
| Crystals 3 ply | $4.5 \times 10^3$ | 4.1 |
| Crystals 5 ply* | $1.5 \times 10^6$ | 6.6 |
| Crystals 5 ply | $< 1.0 \times 10^1$ | $< 1.4$ |

FIG. 34

MRSA Results

20% not as Effective

|  | CFU / Coupon | Log Density |
|---|---|---|
| Cloth | $2.0 \times 10^5$ | 5.7 |
| Cloth | $2.2 \times 10^6$ | 6.8 |
| 3 ply metal | $5.7 \times 10^7$ | 8.2 |
| 3 ply metal | $7.9 \times 10^6$ | 7.3 |
| 5 ply metal | $2.7 \times 10^4$ | 4.9 |
| 5 ply metal | $2.2 \times 10^5$ | 5.8 |
| Glass slide | $1.5 \times 10^7$ | 7.6 |
| Glass slide | $2.2 \times 10^7$ | 7.8 |
| Crystals 3 ply | $4.6 \times 10^8$ | 9.1 |
| Crystals 3 ply | $3.0 \times 10^8$ | 8.9 |
| Crystals 5 ply | $5.7 \times 10^6$ | 7.2 |
| Crystals 5 ply | $9.8 \times 10^7$ | 8.4 |

FIG. 35

MRSA Results
30% Concentration Very Effective

| Sample ID | CFU on Coupon | Log Density | |
|---|---|---|---|
| 5. cloth | <1.0 x 10¹ | <1.4 | no colonies |
| 6. cloth | 7.1 x 10² | 3.3 | |
| 7. 3 ply SS | 1.2 x 10³ | 3.5 | |
| 8. 3 ply SS | 2.4 x 10³ | 3.8 | |
| 9. 5 ply SS | 3.2 x 10³ | 3.9 | |
| 10. 5 ply SS | 2.3 x 10³ | 3.8 | |

* Sample Size: 75mm x 25mm
* Culture Medium: R2A, Soybean Casein Digest Broth
* Neutralizer: Dey-Engley Broth
* Culture Media: Nutrient Agar
* Batch Phase: 6 Hours
* Continuous Flow Phase: 48 hours CFU: Colony Forming Units is estimation of # viable bacteria
Coupon is the article of cloth or stainless steel mesh
Log Density is calculation of biofilm present

FIG. 36

Pseudomonas aeruginosa
Greater than 99.9% kill in 30 minutes

| Organism: *Pseudomonas aeruginosa* | | | ATCC: 700888 | |
|---|---|---|---|---|
| Initial Inoculum Concentration (CFU / 1.0 mL) | | | $1.3 \times 10^8$ | |
| | Glass Slide (Control) | | 30% PCA in 70% IPA | |
| CFU / Sample | Replicate 1 | Replicate 2 | Replicate 1 | Replicate 2 |
| 30 Minute Contact Time | $1.8 \times 10^{10}$ | $3.0 \times 10^{10}$ | $1.5 \times 10^{6}$ | $2.4 \times 10^{7}$ |
| 30 Minute Contact Time (Mean) | $2.4 \times 10^{10}$ | | $1.2 \times 10^{7}$ | |
| Log Reduction at 30 Minutes | 3.3 | | | |
| 60 Minute Contact Time | $2.5 \times 10^{10}$ | $2.2 \times 10^{10}$ | $2.4 \times 10^{5}$ | $3.0 \times 10^{5}$ |
| 60 Minute Contact Time (Mean) | $2.4 \times 10^{10}$ | | $1.5 \times 10^{5}$ | |
| Log Reduction at 60 Minutes | 2.2 | | | |

FIG. 37

MRSA
Greater than 90% kill in 30 minutes

| Organism: *Staphylococcus aureus* (MRSA) | | | ATCC: 33591 | |
|---|---|---|---|---|
| Initial Inoculum Concentration (CFU / 1.0 mL) | | | | $2.1 \times 10^9$ |
| | | CFU / Sample | | |
| | Glass Slide (Control) | | | 30% PCA |
| 30 Minute Contact Time | $6.9 \times 10^7$ | $5.0 \times 10^7$ | $2.7 \times 10^8$ | $3.2 \times 10^6$ |
| 30 Minute Contact Time (Mean) | $6.0 \times 10^7$ | | | $3.0 \times 10^6$ |
| Log Reduction at 30 Minute | 1.3 | | | |
| 60 Minute Contact Time | $2.3 \times 10^7$ | $2.7 \times 10^7$ | $1.7 \times 10^8$ | $3.8 \times 10^6$ |
| 60 Minute Contact Time (Mean) | $2.5 \times 10^7$ | | | $2.0 \times 10^6$ |
| Log Reduction at 60 Minute | 1.1 | | | |

FIG. 38

Pseudomonas aeruginosa
30% PCA Single Spray on Existing Biofilms

Inoculum on glass slide
10 million organisms

RESULTS
Log reduction with PCA at 30 minutes: 3.3
Log reduction with PCA at 60 minutes: 2.2
99.9% Reduction

FIG. 40

Staphylococcus aureus ATCC 33591
30% PCA Single Spray on Existing Biofilms Inoculums on glass slide
10 million organisms allowed to grow RESULTS
30 minutes: 60 million to 3 million
60 minutes: 25 million to 2 million
90% reduction

FIG. 41

Reagent Composite Comparisons
Number No Growth Culture Post Treatment

| Reagent | Aerobic | Anaerobic |
|---|---|---|
| Chloroprep | 21/23 | 19/23 |
| Betadine | 6/11 | 7/11 |
| 70% IPA | 16/23 | 12/23 |
| PCA* | 32/36 | 24/35 |

*Did not include 1% PCA results

FIG. 42

Result Summary
% of No Growth

| Reagent | Aerobic | Anaerobic |
|---|---|---|
| Chloroprep | 91% | 82% |
| Betadine | 55% | 64% |
| 70% IPA | 70% | 52% |
| PCA | 89% | 69% |

FIG. 43

ANTIMICROBIALS AND METHODS OF USE THEREOF

CROSS-REFERENCE TO RELATED APPLICATIONS

This application is a divisional of U.S. application Ser. No. 15/484,827, which is a continuation-in-part of U.S. application Ser. No. 15/189,510, filed Jun. 22, 2016, which is a divisional of U.S. application Ser. No. 14/264,553, filed Apr. 29, 2014, now U.S. Pat. No. 9,498,413, issued Nov. 22, 2016, which claims the benefit under 35 U.S.C. § 119(e) of U.S. Provisional Application No. 61/818,275, filed May 1, 2013, the disclosures of which are incorporated, in their entirety, by this reference.

FIELD OF THE INVENTION

The present invention generally relates to antimicrobial compositions, methods for promoting healing of a wound and more specifically to methods and compositions including the administration of an anthocyanin or an anthocyanidin or metabolites thereof for promoting wound healing by reducing or preventing microbial growth and inducing the activation of growth hormones. Pharmaceutical and nutraceutical compositions containing anthocyanin or anthocyanidins or metabolites thereof suitable for administration to a mammal for promoting or inducing wound healing are also described.

The inventions provided herein also relate to compositions and methods of sanitizing (skin antiseptic) or sterilizing solid surfaces, porous or semi-porous or cloth like surfaces, such as materials or cloth or bandages. Also provided herein are compositions and methods for killing bacterial biofilms, which may be present on implantable devices, solid surfaces, porous or semi-porous, or cloth-like material.

BACKGROUND OF THE INVENTION

There are many illnesses and conditions which are effectively treated by the application of suitable antimicrobial agents. Many microorganisms, however, are increasingly difficult to treat because of resistance or allergic reactions to current antimicrobial agents. The development of resistance is due in part to overuse of the antibiotic and subsequent bacteria mutation. (Blaser, M. Antibiotic overuse: Stop the killing of beneficial bacteria Nature 476, 393-394 (25 Aug. 2011).

The Centers for Disease Control and Prevention (CDC) estimated at least 2 million people in the United States become infected with bacteria that are resistant to antibiotics and at least 23,000 people die each year as a direct result of these infections. (Antibiotic Resistance Threats in the United States, 2013, Centers for Disease Control and Prevention, Atlanta, Ga., USA 2013). The CDC report classified three microorganisms with an antibiotic resistance threat level of urgent in the United States and twelve microorganisms with an antibiotic resistance threat level of serious. Specifically, *Clostridium difficile*, Carbapenem-resistant Enterobacteriaceae (CRE) and drug resistant *Neisseria gonorrhoeae* (cephalosporin resistance) are classified by the CDC as urgent because they require urgent public health attention to identify infections and to limit transmission. Of these, the CDC states "*Clostridium difficile* is the most frequent etiologic agent for health-care-associated diarrhea. In one hospital, 30% of adults who developed health-care-associated diarrhea were positive for *C. difficile*. Risk factors for acquiring *C. difficile*-associated infection include a) exposure to antibiotic therapy, particularly with beta-lactam agents; b) gastrointestinal procedures and surgery; c) advanced age; and d) indiscriminate use of antibiotics. Of all the measures that have been used to prevent the spread of *C. difficile*-associated diarrhea, the most successful has been the restriction of the use of antimicrobial agents." (Sehulster L, Centers for Disease Control and Prevention, Guidelines for environmental infection control in healthcare facilities. MMWR 2003; 52(RR10); 1-42). *C. difficile* is an anaerobic, gram-positive bacterium capable of sporulating when environmental conditions no longer support its continued growth. The capacity to form spores enables the organism to persist in the environment (e.g., on dry surfaces or in soil) for extended periods of time. Environmental contamination by this microorganism is well known, especially direct exposure to contaminated patient-care items and high-touch surfaces in patients' bathrooms have been implicated as sources of infection. The CDC stated, "More needs to be done to prevent *C. difficile* infections (CDIs). Major reductions will require antibiotic stewardship along with infection control applied to nursing homes and ambulatory-care settings as well as hospitals. State health departments and partner organizations have shown leadership in preventing CDIs in hospitals and can prevent more CDIs by extending their programs to cover other health-care settings." (CDC, Vital Signs; Preventing *Clostridium difficile* infections, MMWR 2012; 61-157-62). Because *C. difficile* spores resist killing by usual hospital disinfectants, an Environmental Protection Agency-registered disinfectant with a *C. difficile* sporicidal label claim should be used to augment thorough physical cleaning.

Twelve serious antibiotic-resistant threats identified in the CDC report include: multidrug-resistant *Acinetobacter*, Drug-resistant *Campylobacter*, Fluconazole-resistant *Candida* (fungus), Extended spectrum β-lactamase producing Enterobacteriacaea (ESBLs), Vancomycin-resistant *Enterococcus* (VRE), Multidrug-resistant *Psuedomonas Aeruginosa*, Drug-resistant Non-typhoidal *Salmonella*, Drug-resistant *Salmonella Typhi*, Drug-resistant *Shigella*, Methicillin-resistant *Staphylococcus auereus* (MRSA), Drug-resistant *Streptococcus pneumonia*, Drug-resistant tuberculosis (MDR and XDR)(Antibiotic Resistance Threats in the United States, 2013, Centers for Disease Control and Prevention, Atlanta, Ga., USA 2013). Of the twelve serious antibiotic-resistant threats identified in the CDC report, Methicillin-resistant *Staphylococcus aureus* (MRSA) is the most frequently identified antimicrobial drug-resistant pathogen in U.S. hospitals. MRSA was one of the first pathogens to develop resistance, first detected the United Kingdom in 1961. In 1999, MRSA was responsible for 37% of fatal cases of sepsis in the UK. Additionally, half of all *S. aureus* infections in the U.S. are resistant to penicillin, methicillin, tetracycline and erythromycin, leaving only vancomycin as an effective agent against *S. aureus*; however, strains with intermediate levels of resistance, termed glycopeptide-intermediate *Staphylococcus aureus* (GISA) or vancomycin-intermediate *Staphylococcus aureus* (VISA), began appearing in the late 1990s and oxazolidinone, (linezolid) resistance in *S. aureus* was reported in 2001. Additionally, community-acquired MRSA (CA-MRSA) has now emerged as an epidemic that is responsible for rapidly progressive, fatal diseases, including necrotizing pneumonia, sepsis, and necrotizing fasciitis. Outbreaks of CA- MRSA infections have been reported in correctional facilities, among athletic teams and military recruits, and in nurseries.

In addition to resistance, current antibiotics also have a limited use due to allergic reactions in many patients (Romano A, Caubet J C. Antibiotic allergies in children and adults: from clinical symptoms to skin testing diagnosis. J Allergy Clin Immunol Pract. 2014 January-February; 2(1): 3-12).

Not only does resistance and allergic reactions to current antimicrobial agents result in increased patient morbidity and even mortality, but ineffectiveness of current antimicrobial agents is also a major expense to society. Surgical infections are costly not only because of cost of treatment, including potentially hospitalization, but also the loss of productive work. This is exemplified in treatment of an infected total knee replacement. The relative incidence of operative infections was reported as 2.0% and 2.4% following total knee surgery. The most common cause of revision total knee surgery (25.2%) is infection. (Bozic K J et al. The epidemiology of revision total knee arthroplasty in the United States. Clin Orthop Relat Res. 2010 January; 468 (1):45-51). The annual cost of infected revisions to U.S. hospitals increased from $320 million to $566 million during the study period and was projected to exceed $1.62 billion by 2020. (Kurtz S M, et al Economic burden of periprosthetic joint infection in the United States. J Arthroplasty. 2012 September; 27(8 Suppl) The average cost of the surgical revision of an infected total knee replacement was $116,383 in the years 2001 through 2007. (Kapadia B H, et al. The Economic Impact of Periprosthetic Infections Following Total Knee Arthroplasty at a Specialized Tertiary-Care Center. J Arthroplasty. 2013 Oct. 17).

There is also a high cost to prophylactic antibiotic treatment prior to and around the time of surgery. (Chaweewannakom U. et al., Cost analysis of peri-operative antibiotic administration in total knee arthroplasty. J Med Assoc Thai. 2012 October; 95 Suppl 10:S42-7; Hebert C K, et al., Cost of treating an infected total knee replacement. Clin Orthop Relat Res. 1996 October; (331):140-5). Furthermore, these costs may not be covered by government insurance in the U.S. especially with the large personal deductibles people have chosen under the Affordable Care Act. This problem already exists in Germany. This is a burden on the patient if they pay. If they do not pay then the cost is shifted to the doctor and the hospital. (Haenle M. et al. Economic impact of infected total knee arthroplasty. Scientific World Journal. 2012; 2012: 1 96515).

Treatment of the failed infected total joint may include repeat surgery, removal of the implant, insertion of an antibiotic impregnated spacer, hospitalization, therapy and return at later date to remove spacer and redo the total joint with hospitalization and long term antibiotics. (Garg P, et al. Antibiotic-impregnated articulating cement spacer for infected total knee arthroplasty. Indian J Orthop. 2011 November; 45(6):535-540).

Fungal infections also are problematic and have become less susceptible to current antimicrobial agents. In hospitalized patients, fungal infections are the fourth common cause of blood stream infection. *Candida albicans* is the major fungal pathogen of humans. (Warren, N G, American Society for Microbiology; 1995. 723; Bachmann, S P, Antimicrobial Agents Chemother, 2002; 46: 3591). It has been reported that mortality rate of patients with catheter related candidemia approaches 40%. (Fux, C A, Trends Microbiol, 2005; 13(1): 34; and Tampakakis, E., Eukaryot Cell, 2009; 8:732). Biofilms of *C. albicans* are capable of holding other micro-organisms and more likely to be heterogeneous with other bacteria and fungi in the environment and on medical devices. (E Tampakakis, A Y Peleg, E Mylonakis. Eukaryot Cell, 2009; 8:732.) Moreover, biofilm cells are significantly less susceptible to antimicrobial agents. As a result, drug therapy for an implant infection may be futile, and often, the only solution is mechanical removal of the implant. (Melissa J J, et al, Antimicrob Agents Chemother. 2009; 53(6): 2638; and Anderson, J B, Nat Rev Microbiol, 2005; 3(7): 547). Biofilm formation also plays an important role in outbreaks of *C. albicans* related infections.

Between 1935 and 1968, 14 different classes of antibiotic were developed. In the 45 years since then, only five have been brought out. No new classes have now been developed since 1987 (last 30 years). Because of this lack of new antibiotics, and because of the acquired resistance to the known antibiotics, there is a continuing need for new antimicrobials and compositions, which are effective in reducing or preventing microorganism growth. The new antimicrobials and compositions can have a broad spectrum of utility without a history of overuse or resistance. The new methods and compositions can be applicable to promoting healing of wounds. In addition, the antimicrobials and compositions would have no known allergic manifestation. Further the new antimicrobials and compositions would be cost effective. There is also a need for antimicrobial compositions that can be effectively used on various surfaces, including high-touch surfaces such as light switches and bathroom fixtures, medical devices, patient-care items, and the like to reduce microbial contamination.

At present, in order to minimize the incidence of perisurgical wound infections the patient is given preoperative antibiotics, intra operative intra venous antibiotic, intraoperative antibiotic wound irrigation. (Heller S, Rezapoor M, Parvizi J. Minimising the risk of infection: a peri-operative checklist. Bone Joint J. 2016 January; 98-B(1 Suppl A):18-22.); (Whiteside L A. Prophylactic peri-operative local antibiotic irrigation. Bone Joint J. 2016 January; 98-B(1 Suppl A):23-6.)

Often antibiotic crystals and/or powder are placed in about the implant and the wound the wound before closure. (Bakhsheshian J, Dandaleh N S, Lam S K, Savage J W, Smith Z A. The use of vancomycin powder in modern spine surgery: systematic review and meta-analysis of the clinical evidence. World Neurosurg. 2015 May; 83(5):816-23); (Molinari R W, Khera O A, Molinari III W J. Prophylactic intraoperative powdered vancomycin and postoperative deep spinal wound infection: 1,512 consecutive surgical cases over a 6-year period. Eur Spine J. 2012 June; 21(Suppl 4): 476-482.)

Attempts have been made by major implant OEM's to coat implants with an antibiotic at time of manufacture. (personal communication from Smith+Nephew Company) but without success. The attempts have been abandoned at the time of this application due to lack of a method and the high barrier cost of 50 to 150 million dollars to perhaps gain FDA approval. In spite of all these measures, peri surgical infections still occur. There is a need for effective means of reducing peri surgical infections following implant surgery, especially ones that at prone to biofilms formation.

Previous clinical studies performed with various skin surface disinfectants have not been successful in decreasing the presence of *Propionibacterium acnes*. The reason is that the regents used were not accompanied by a vehicle that would penetrate intact human skin. (Lee M J, Pottinger P S, Butler-Wu S, Bumgarne R E, Russ S M, Mattsenlll F A. *Propionibacterium* Persists in the Skin Despite Standard Surgical Preparation. J Bone Joint Surg Am, 2014 Sep. 3; 96 (17): 1447-1450); (Saltzman M D, Nuber G W, Gryzlo S M, Mareck G S, Koh J L. Efficacy of Surgical Preparation Solutions in Shoulder Surgery. J Bone Joint Surg Am, 2009 Aug. 1; 91 (8): 1949-1953); (McLellan E, Rownsend R, Parsons H K. Evaluation of ChloraPrep (2% chlorhexidine gluconate in 70% isopropyl alcohol) for skin antiseptic in preparation for blood culture collection. Journal of Infection, Volume 57, Issue 6, 459-463). This is likely due to the fact that P. acnes normally reside deep in the skin surface within the hair follicles and/or sebaceous glands. Therefore, it necessary to have a composition of matter in treating potential pathogens on the human skin, especially P. acnes that contains within the vehicle a property than enhances skin penetration. Nakatsuji et al showed that the microbiota extends within the dermis, therefore, enabling physical contact between bacteria and various cells below the basement membrane. These observations show that normal commensal bacterial communities directly communicate with the host in a tissue previously thought to be sterile. (Nakatsuji T, Chiang H I, Jiang S B, Nagarajan H, Zengler K, Gallo R L. The microbiome extends to subepidermal compartments of normal skin. Nat Commun. 2013; 4:1431.) Zeeuwen et. al. showed the bacterial communities of the surface of human skin, mostly under static conditions in healthy volunteers differs from what is found following skin injury. The dynamics of re-colonization of skin microbiota following skin barrier disruption by tape stripping as a model of superficial injury showed microbiome of the deeper layers, rather than that of the superficial skin layer, may be regarded as the host indigenous microbiome. (Zeeuwen P L, Boekhorst J, van den Bogaard E H, de Koning H D, van de Kerkhof P M, Saulnier D M, van Swam I I, van Hijum S A, Kleerebezem M, Schalkwijk J, Timmerman H M. Microbiome dynamics of human epidermis following skin barrier disruption. Genome Biol. 2012 Nov. 15; 13(11):R101.) Therefore, there is a need for a composition that has skin penetration properties to deliver an effective skin antiseptic regent and there remains a need for a composition useful in treating potential pathogens on the human skin, especially P. acnes that contains within the composition a substances than enhances skin penetration.

Donlan's comprehensive review of biofilms reported that when antibiotics were first developed, the pathologic bacteria were singular and free floating. They were characterized as planktonic. Subsequently bacteria have developed resistance by mutation and biofilms formation. Leeuwenhoek first observed a biofilm is an assemblage of surface-associated microbial cells that is enclosed in an extracellular polymeric substance matrix. (Donlan R M. Biofilms: Microbial Life on Surfaces. Emerg Infect Disease. 2002; 8(9): 881-890). In addition, Donlan's review stated that biofilms are highly resistant to most antimicrobial agents and disinfectants (Donlan R M. Role of biofilms in antimicrobial resistance. ASAIO J. 2000; 46:S47-52.). In addition, organisms within biofilms can readily acquire resistance through the transfer of resistance plasmids. Such resistance could be especially acute in the health-care environment for patients with colonized urinary catheters and collection bags. Many of the enteric organisms shown to colonize urinary catheters carry plasmids encoding resistance to multiple antimicrobial agents (Sedor J, Mulholland S G. Hospital acquired urinary tract infections associated with the indwelling catheter. Urol Clin North Am. 1999; 26:821-8).

Transfer of plasmids within biofilms has been well established (as already discussed). Resistant organisms such as methicillin-resistant Staphylococcus aureus have also been shown to form biofilms (Murga R, McAllister S, Miller J M, Tenover F, Bell M, Donlan R M. Effect of vancomycin treatment of methicillin-resistant S. aureus (MRSA) biofilms on central venous catheters in a model system. Poster No. C276 presented at the 2001 American Society for Microbiology Annual Meeting, Orlando, Fla., May 23, 2001.) Biofilms may form on a wide variety of surfaces, including living tissues, indwelling medical devices, industrial or potable water system piping, or natural aquatic systems. An implant in the body, i.e. total joint, typically has the biofilms attach to the implant and then the bacteria colony grows. A common example of biofilms is dental plaque. It requires physical removal with a tooth brush. Physical removal is not possible when an implant is inside the body; total joint, catheter, pacemaker, etc. Therefore the must be another way to arrest their formation by attachment to an implant and or foreign material in the body. The best way, and is the subject of the invention, is to coat the implant with material the resists the biofilms attachment as well as destroys the biofilms and bacteria upon contact.

Donlan reported the following: "For most of the history of microbiology, microorganisms have primarily been characterized as planktonic, freely suspended cells and described on the basis of their growth characteristics in nutritionally rich culture media. Rediscovery of a microbiologic phenomenon, first described by van Leeuwenhoek, that microorganisms attach to and grow universally on exposed surfaces led to studies that revealed surface-associated microorganisms (biofilms) exhibited a distinct phenotype with respect to gene transcription and growth rate. These biofilm microorganisms have been shown to elicit specific mechanisms for initial attachment to a surface, development of a community structure and ecosystem, and detachment." (Donlan, R M Biofilms: Microbial Life on Surfaces. Emerging Infectious Diseases. Vol 8 (9) September 2002).

Characklis et al. noted that the extent of microbial colonization appears to increase as the surface roughness increases. This is because shear forces are diminished, and surface area is higher on rougher surfaces. Rough surfaces are common to total joint implants for the purpose of fixation for bony ingrowth. Therefore there is compelling need for method to coat a total joint implant. (Characklis W G, McFeters G A, Marshall K C. Physiological ecology in biofilm systems. In: Characklis W G, Marshall K C, editors. Biofilms. New York: John Wiley & Sons; 1990. p. 341-94).

Donlan reported that biofilms are highly resistant to most antimicrobial agents and disinfectants. (Donlan R M. Role of biofilms in antimicrobial resistance. ASAIO J. 2000; 46:S47-52). Resistant organisms such as methicillin-resistant Staphylococcus aureus (MRSA) have also been shown to form biofilms. Therefore there is a need for biofilms destroying reagent for MRSA including, but beyond the application to catheters. (Murga R, McAllister S, Miller J M, Tenover F, Bell M, Donlan R M. Effect of vancomycin treatment of methicillin-resistant S. aureus (MRSA) biofilms on central venous catheters in a model system. Poster No. C276 presented at the 2001 American Society for Microbiology Annual Meeting, Orlando, Fla., May 23, 2001).

SUMMARY OF THE INVENTION

In its various embodiments, the present invention provides generally for compositions and methods for reducing or preventing microbial growth, which are particularly useful for treating and promoting the healing of wounds. Specifically, the present invention provides methods and pharmaceutical and nutraceutical compositions that reduce or substantially eliminate potentially pathologic microbes.

In one embodiment, a method of promoting healing of a wound in a mammal is provided; comprising administering an anthocyanin or an anthocyanidin to the mammal in need of such treatment a therapeutically effective amount of the anthocyanin or anthocyanidin composition or compound wherein microbial growth is reduced and local growth hormone activity is optimized.

In a further embodiment, a method of promoting healing of a wound in a mammal is provided; comprising administering an anthocyanin metabolite or an anthocyanidin metabolite to the mammal in need of such treatment a therapeutically effective amount of the metabolite or anthocyanidin metabolite compositions wherein microbial growth is reduced and local growth hormone activity is optimized.

Further, the invention provides methods and compositions that effectively deliver the compositions to the affected wound. The present invention provides compositions and methods for use in the treatment of a variety of wound problems, including but not limited to, burns, pressure wounds, abrasions, diabetic wounds, peri-surgical and skin infections. The present invention provides compositions and methods for use in the treatment of a variety of infections, including those from blood transfusions. Preferably, the therapeutic compositions and compounds are administered orally or topically; however, the therapeutic compositions and compounds may be administered by any conventional route including, for example, oral, topical, buccal, injection, pulmonary, intravenous, inhalant, subcutaneous, sublingual, or transdermal. Those of skill in the art can readily determine the various parameters and conditions for producing these compositions or formulations without resort to undue experimentation.

In one aspect, the present invention provides a pharmaceutical composition for promoting wound healing, comprising: a) an anthocyanin; or b) anthocyanidin. By way of example, the anthocyanin can be selected from cyanidin-3-glucoside or delphinidin-3-glucoside, cyanidin-3-galactoside, and pelargonidin-3-galactoside. Also by way of example, the anthocyanidins can be selected from cyanidin, delphinidin, pelargonidin, malvidin and petunidin.

In one aspect, for example, the present disclosure provides a pharmaceutical composition comprising: a) an anthocyanin metabolite; or b) an anthocyanidin metabolite. In another aspect, the present invention provides for a pharmaceutical composition for promoting wound healing, comprising: a) an anthocyanin metabolite; or b) and anthocyanidin metabolite. By way of example, metabolites can be selected from protocatechuic acid and 2, 3, 4 trihydroxybenzaldehyde. In yet another aspect, the present disclosure provides a pharmaceutical composition comprising: a) a metabolite of an anthocyanin metabolite; or b) a metabolite of an anthocyanidin metabolite. By way of example, the metabolites are metabolites selected from protocatechuic acid, and 2, 3, 4 trihydroxybenzaldehyde.

Further by way of example, the pharmaceutical composition can comprise: a) an anthocyanin; or b) an anthocyanidin; and c) a pharmaceutically acceptable carrier. Further by way of example, the pharmaceutical composition can comprise: a) an anthocyanin metabolite; or b) an anthocyanidin metabolite; and c) a pharmaceutically acceptable carrier. By way of example, the pharmaceutically acceptable carrier can be selected from, but not limited to, any carrier, diluent or excipient compatible with the other ingredients of the composition.

Further by way of example, the pharmaceutical composition can comprise: a) an anthocyanin; and/or b) an anthocyanidin; and/or c) a pharmaceutically acceptable carrier; and/or d) an acceptable delivery carrier. By way of example, the delivery carrier can be formulated and administered as known in the art, e.g., for topical, oral, buccal, injection, intravenous, inhalant, subcutaneous, sublingual or transdermal Further, said topical delivery carrier may be formulated and administered to any surface, including but not limited to skin, bone, synovium, cartilage, and implants. By way of example, the acceptable delivery carrier can be selected from any dermal or transdermal carrier compatible with the other ingredients of the composition. In some embodiments, the acceptable delivery carrier is a biodegradable microsphere or a slow release bioadsorbable material. By way of example, the acceptable delivery carrier can be selected from 50/50 D, L lactide/glycolide or 85/15 D, L lactide/glycolide, both of which are amorphous physically and, therefore, are non-reactive when used as a carrier in a composition that is delivered in or to the body.

In yet another aspect and in other embodiments, the anthocyanidin provided in any recited composition is provided less than 200 mM and in other embodiments about 100 mM. In some embodiments, the anthocyanin or anthocyanidin provided in any recited composition or method of use is provided in a range of between 10 to 200 mM. In other embodiments, the anthocyanin metabolite or anthocyanidin metabolite provided in any recited composition or method of use is provided in a range of between 20 to 200 mM. In yet other embodiments, the anthocyanin, anthocyanidin, or metabolites thereof provided in any recited composition or method of use is provided in a range of between 20 to 100 mM. In yet other embodiments, the anthocyanin, anthocyanidin, or metabolites thereof provided in any recited composition or method of use is provided in a range of between 20 to 50 mM. In some embodiments, the metabolite is provided in any recited composition less than 100 mM and in others at 25 mM.

In one aspect, for example, the present disclosure provides for an antimicrobial composition comprising: a) an anthocyanin metabolite; or b) an anthocyanidin metabolite. By way of example, metabolites can be selected from protocatechuic acid, 2, 3, 4 trihydroxybenzaldehyde. By way of example, the anthocyanin, anthocyanidin and metabolites thereof can have broad spectrum activity against disease-causing microbes. In another aspect of the present invention a method of treating a wound of an individual is provided, comprising administering any of the recited pharmaceutical compositions by topical application, transdermal, buccal, oral, gavage, and injection or intravenous.

The present disclosure also provides for methods for reducing microorganisms on any surface or liquid, comprising contacting a surface or liquid with any of the recited compositions.

The present disclosure also provides for compositions and methods for reducing microorganisms in foods comprising contacting a food with any of the recited compositions.

The invention also provides a method of killing methicillin resistant *Staphylococcus aureus* (MRSA) and *Pseudomonas aeruginosa* biofilm colonies comprising spraying a solution of up to 30% PCA in 70% isopropyl alcohol on a surface containing a biofilm. The surface is a solid surface, porous or semi-porous, or a cloth-like surface.

Also provided a bandage or wound dressing having a solution of PCA or 2, 4, 6 trihydroxybenzaldehyde (246 THBA) or mixtures thereof impregnated thereon, and methods of preparing same.

The invention provides a method of treating a solid surface, porous or semi-porous, or a cloth-like surface to sanitize, sterilize, reduce bacterial growth or inhibit growth of microorganisms, the method comprising treating the solid surface with a solution of PCA or 2, 4, 6 trihydroxybenzaldehyde (246 THBA) or mixtures thereof, or in the case of porous or semi-porous surface or cloth-like surface, treating with a solution of PCA or PCA crystals.

Included is a method of treating a medical device or surgical implant to sanitize, sterilize, reduce bacterial growth or inhibit growth of microorganisms, the method comprising treating the medical device or surgical implant with a solution of PCA or 2, 4, 6 trihydroxybenzaldehyde (246 THBA) or a mixture thereof.

An embodiment of the invention includes a method of treating skin of a mammal to kill microorganisms on the skin, the method comprising treating the skin with a solution of PCA or 2, 4, 6 trihydroxybenzaldehyde (246 THBA) or a mixture thereof to kill microorganism on the skin. The skin can be treated before a surgical procedure or after a surgical procedure.

Another embodiment of the invention provides a method of killing P. acnes on the skin of a patient, the method comprising applying a solution of PCA or 2, 4, 6 trihydroxybenzaldehyde (246 THBA) or a mixture thereof to the skin of the patient to kill the P. acnes.

The invention also includes a solution comprising 20-30% PCA, and essential oils; as peppermint or lemon oil etc., propylene glycol and isopropyl alcohol. In addition, because liposomes have skin penetration properties they may be used in dermal applications with the compositions of the invention.

The present invention also provides a covering or bandage for administering antimicrobial compositions to a wound, wherein the antimicrobial compositions is an element of the covering or bandage. Methods for promoting healing of a wound and more specifically to methods and compositions including the application of an anthocyanin or an anthocyanidin or metabolites thereof in the form of a covering or bandage for promoting wound healing by reducing or preventing microbial growth and inducing the activation of growth hormones are described. Pharmaceutical compositions containing anthocyanin or anthocyanidins or metabolites thereof suitable for transdermal administration to a mammal for promoting or inducing wound healing are also described.

BRIEF DESCRIPTION OF THE DRAWINGS

FIG. 1 provides the minimum, maximum and optimum pH for growth of microorganisms. Acidic environments retard proliferation of various bacteria. Anthocyanins, anthocyanidins and main metabolites are unstable relative to basic pH; thus, anthocyanins, anthocyanidins and main metabolites thereof have the potential to lower the pH of wound tissue as well as any surfaces and act as bactericidal or bacteriostatic.

FIG. 6 is a table providing a summary of the effectiveness of certain anthocyanins, anthocyanidins and a metabolite, including bactericidal or bacteriostatic activity. During this test, the purity, concentrations and molecular weight of these test substances (compounds) were known. The carrier was water and the dose was accurately calculated. Delphinidin limited growth against *C. perfringens, S. aureus,* and MRSA. Pelargonidin limited growth of *P. acnes, C. perfingens, S. aureus,* MRSA, and *S. pyogenes.* Cyanidin CI was effective against *C. difficile, C. prefringens, S. aureus* ATCH 6538, *S. aureus* (MRSA) ATCH 33591, *S. mutans,* and *S. pyogenes.* A proprietary formulation of cyanidin-3-glucoside (approximately 28% C3G by weight) had limited effectiveness during this study (18-24 hours for aerobes; 48 hours for anaerobes (*C. albacans* and *L. casei*); however, this C3G formulation, was effective against *P. acnes, E. coli,* MRSA, *K. pneumoniae* and *P. aeruginosa.* Protocathechuic acid (PCA), the main metabolite from anthocyanins and anthocyanidins, was effective against all bacteria tested as well as *C. albicans* and *K. pneumonia.* Importantly for skin wound treatment, PCA was effective against *S. aureus* 6538 and 33591 (MRSA) and *P. aeruginosa.* PCA was also effective on *C. albicans,* which is important considering its ability to form biofilms and difficulty in treating *C. albicans* when existing with a catheter or implant.

FIG. 7 is a table summarizing in vitro test results of 2, 4, 6 Trihydroxybenzaldehyde and demonstrating its ability to act as an antimicrobial, including as a bactericidal or bacteriostatic. Specifically, 2, 4, 6 Trihydroxybenzaldehyde was effective against *E. coli, K. pneumonia, P. aeruginosa, S. aureus* 6538 and 33591 (MRSA); further it was effective against a fungi, *Aureobasidium pullulans,* ATCC 15233.

11B shows the results of a rodent back skin study to determine the effects of PCA and C3G on the local growth hormones in untreated skin wounds of rodents. A concentration of 25 mM PCA increased local growth hormone levels of TGF-Beta at the site of the untreated skin wound.

FIG. 32 provides a chart studying the effectiveness of anthocyanin and anthocyanidin metabolites against various microbes, including *P. acnes, C. difficile, E. coli* 8739 and 43895, *S. Aureus* 6538, 33591, *P. Aeruginosa* 9027, MRSA 51625 and *Legionella* 43662, methicillin resistant *staphylococcus epidermis* (MRSE), including MRSE ATCC 51625, and others.

FIG. 33 provides a chart summarize results of testing PCA against *Pseudomonas* biofilm.

FIG. 34 provides a chart summarize results of testing PCA against *Pseudomonas* biofilm.

FIG. 35 provides a chart summarize results of testing PCA against MRSA biofilm.

FIG. 36 provides a chart summarize results of testing PCA against MRSA biofilm.

FIG. 37 provides a chart summarize results of testing PCA against *Pseudomonas* biofilm.

FIG. 38 provides a chart summarize results of testing PCA against MRSA biofilm.

FIG. 40 shows the results for a single spray of 30% PCA in isopropyl alcohol on 10 million biofilms colonies of *Pseudomonas aeruginosa*.

FIG. 41 shows the concentration of 30% has lesser effect on MRSA, but still 90%.

FIG. 42 provides a composite of the results based only for no growth cultures following treatment by each solution. *Note that the 1% PCA was not included.

FIG. 43 provides the summation percentages of "no growth."

DETAILED DESCRIPTION OF THE INVENTION

Definitions

Figure 2:
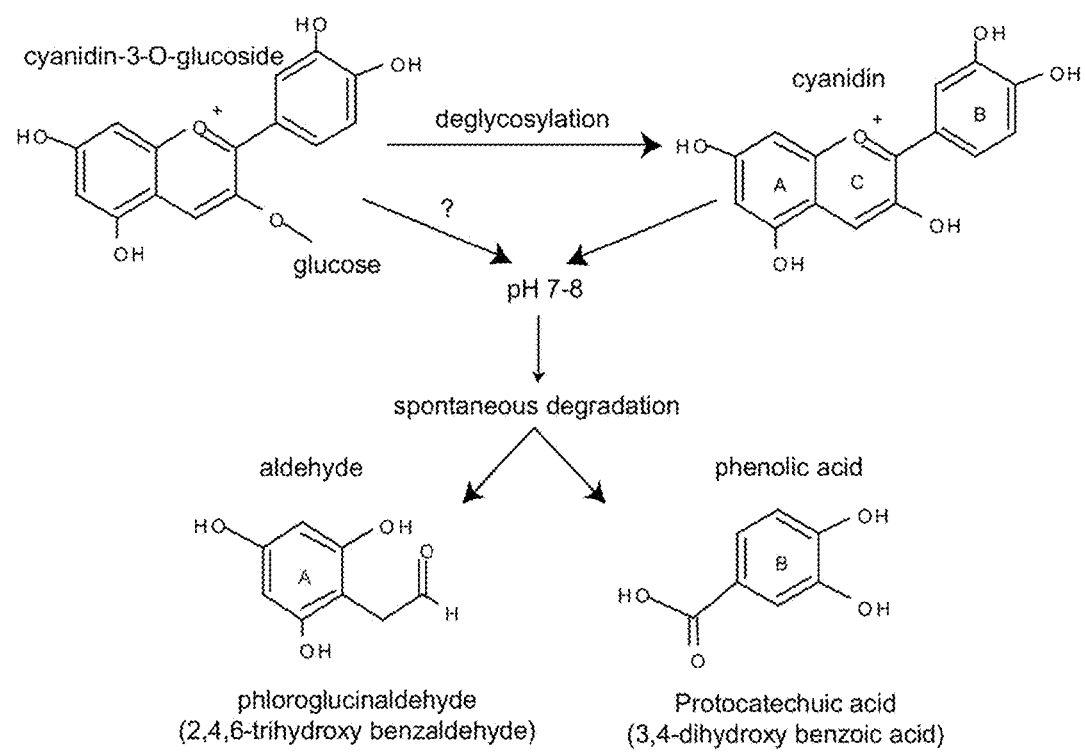
FIG. 2 is the metabolic pathway of cyanidin-3-glucoside (C3G) and includes the chemical structures of cyanidin-3-glucoside and cyanidin and their metabolites.
Figure 3:
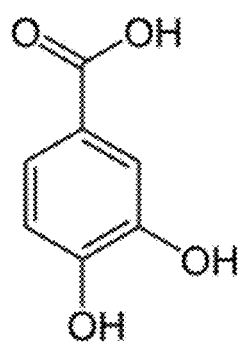
FIG. 3 is the chemical structure of Protocatechuic acid (PCA), a dihydroxybenzoic acid, a type of phenolic acid. It is a major metabolite of antioxidant polyphenols found in certain plants, including green tea.
Figure 4:
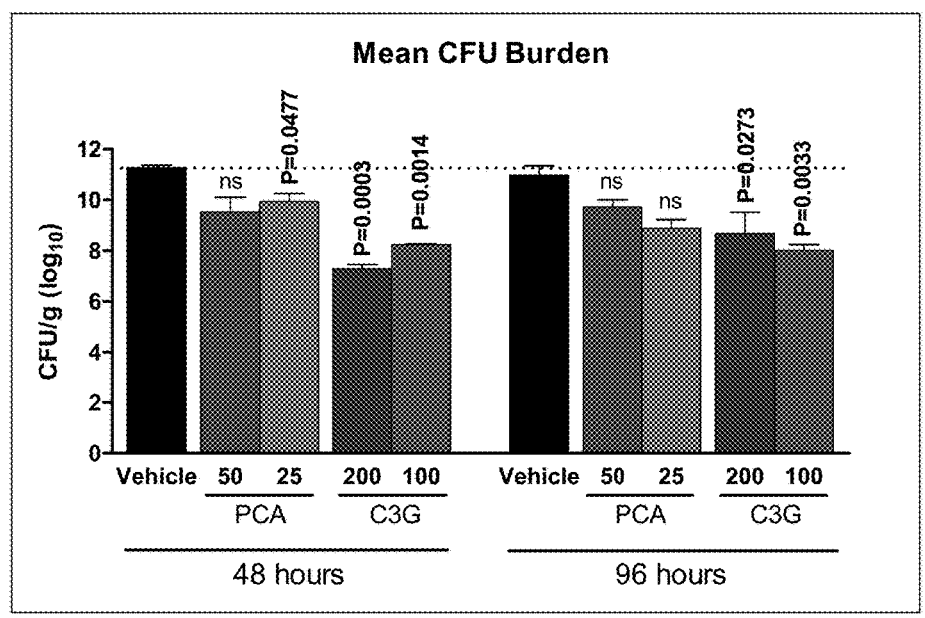
FIG. 4 compares concentrations of C3G and PCA to determine optimal effective concentrations. Bacterial burdens for P. aeruginosa were compared after treatment with C3G or PCA at 48 and 96 hours. A concentration of PCA 25 mM was effective to reduce the bioburden with statistical significance at 48 hours. C3G at 100 and 200 mM concentrations were effective at reducing the bioburden at 48 and 96 hours.
Figure 5:
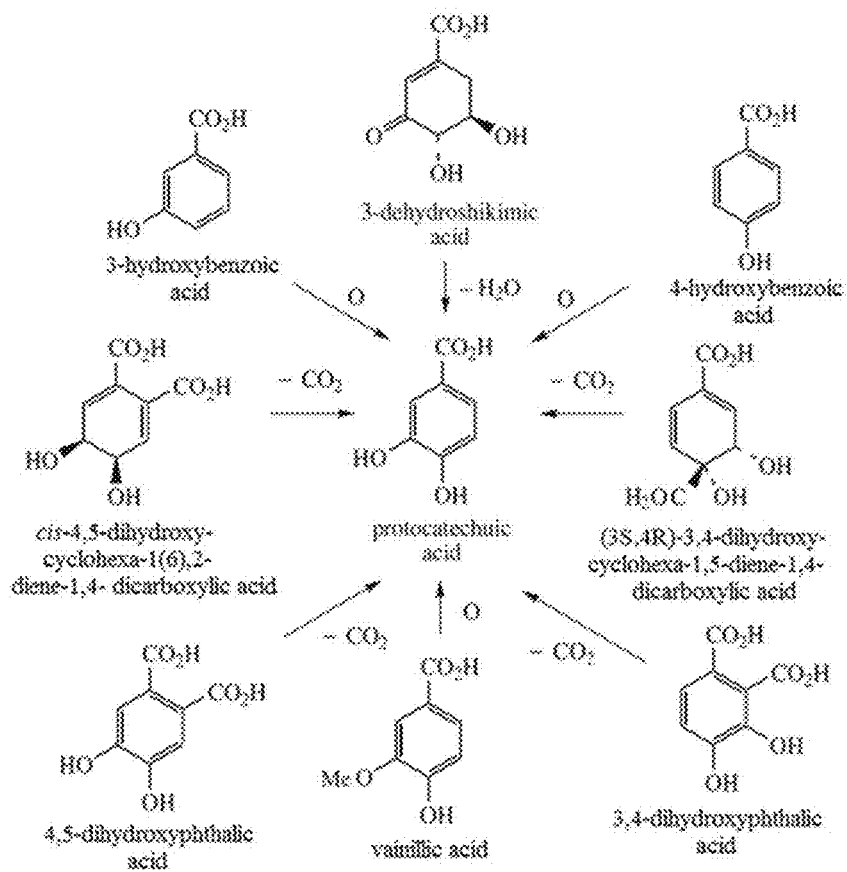
FIG. 5 is a chart disclosing potential sources of PCA.

Unless otherwise indicated, all technical and scientific terms used herein shall have the same meaning as is commonly understood by one of ordinary skill in the art to which the disclosed subject matter belongs. Unless otherwise indicated, the following definitions are applicable to this disclosure. All publications referred to throughout the disclosure are incorporated by reference in their entirety. To the extent any definition or usage provided by any document incorporated herein by reference conflicts with the definition or usage provided herein, the definition or usage provided herein controls.

As used in the specification and claims, the singular forms "a," "an," and "the" include plural referents unless the context clearly dictates otherwise. Thus, for example, reference to "a composition" includes mixtures or combinations of two or more such compositions.

Throughout the specification and claims, the word "comprise" and variations of the word, such as "comprising" and "comprises," means "including but not limited to," and is not intended to exclude, for example, other components, extracts, additives, or steps. It is also contemplated that embodiments described as "comprising" components, the invention also includes those same inventions as embodiments "consisting of" or "consisting essentially of."

Ranges can be expressed herein as "approximately" or from "about" one particular value, and/or to "about" another particular value. When such a range is expressed, another embodiment includes from the one particular value and/or to the other particular value.

A weight percent of a reagent, component, or compound unless specifically stated to the contrary, is based on the total weight of the reagent, component, composition or formulation in which the reagent, component, or compound is included, according to its usual definition.

By "reduce" or other forms of the word, such as "reducing" or "reduction," is meant decrease or lower a characteristic (e.g., inflammation, growth or viability of microorganisms).

By "promote" or other forms of the word, such as "promoting," is meant to induce a particular event or characteristic, or delay the development or progression of a particular event or characteristic, or to minimize the chances that a particular event or characteristic will occur.

"Treat" or other forms of the word, such as "treating," "treatment" or treated," is used here to mean to administer a composition or to perform a method in order to induce, reduce, eliminate, and prevent a characteristic (e.g., inflammation, growth or viability of microbes). It is generally understood that treating involves providing an effective amount of the composition to the mammal or surface for treatment.

The term "vehicle" or "vehicle carrier" as used herein refers to mean the manner in which the reagents or compositions may be delivered, including as a liquid, salve, soap, foam, cream, solution, gel, spray, powder, wipes, antibacterial treatments, wipes and the like.

The term "wound" or "wound associated condition" as used herein refers to a medical condition when the integrity of any tissue is compromised (e.g., burns, skin breaks, bone breaks, muscle tears, tendon injuries punctures, surgical incision sites, microdermabrasion site, skin graft site,). A wound may be caused by any act, infectious disease, underlying condition, fall, or surgical procedure. A wound may be chronic, such as skin ulcers caused by diabetes mellitus, or acute, such as a cut or puncture from a sharp object, an animal bite or a gunshot.

The term "growth factors" or "local growth factors" include but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-$\beta$, TGF-$\alpha$, and collagen growth factors, and/or biologically active derivatives of these growth factors.

By "bactericidal" or "antimicrobial" is meant the ability to effect (e.g., eliminate, inhibit decrease, or prevent) microorganism growth, viability, and/or survival at any concentration. It also means kill the microorganism.

By "bacteriostatic" is meant the ability to effect (e.g., stabilize or prevent future growth or prevent new growth) microorganism growth at any concentration. A bacteriostatic compound, agent or reagent does not eliminate or kill the bacteria.

By "additive" or "food additive" is meant to the use as a component of any food (including any substance intended to use in producing manufacturing, packing, processing, preparing, treating, packaging, transporting, or holding food).

By "antiseptic" is meant an antimicrobial reagent or composition that is applied to any surface, including skin or tissue, to effect (e.g., eliminate, inhibit, decrease or prevent) microorganism growth, viability, and/or survival.

By "disinfect" or other forms of the word, such as "disinfectant" or "disinfecting," is meant decrease or lower a characteristic (e.g., eliminate, reduce, inhibit, decrease, or prevent) microorganism growth, viability or survival at any concentration. It is generally understood that disinfect involves providing an effective amount of the composition to any surface, but particularly solid surfaces, whether smooth or porous or semi-porous, or cloth-like surfaces.

By "sanitize" or other forms of the word, such as "sanitizer" or "sanitizing," is meant decrease or lower a characteristic (e.g., eliminate, reduce, inhibit, decrease, or prevent) microorganism growth, viability or survival at any concentration. It is generally understood that sanitizing involves providing an effective amount of the composition to any surface. Further, it is generally understood that sanitizing solutions and sanitizing components are those solutions that may be safely used on food-processing equipment and utensils and on other food-contacting conditions.

By "sterilize" it is meant to kill microbes on the article being sterilized. Sterilize and sterilization include cold sterilization methods.

By "isolated" or "an isolate" as it refers to either the compounds or reagents described herein means not 100% by weight but rather approximately 95% to 97% of the compound or reagent by weight.

The term "alkyl" as used herein is a branched or unbranched hydrocarbon group of 1 to 20 carbon atoms. Non limiting examples include methyl, ethyl, n-propyl, isopropyl, n-butyl, isobutyl, t-butyl, pentyl, hexyl, heptyl, octyl, nonyl, decyl, dodecyl, tetradecyl, hexadecyl, octadecyl, eicosyl, tetracosyl, and the like. Further, the alkyl group can also be substituted or unsubstituted.

The term "alkoxy" or "alkyoxy group" as used herein refers to a branched or unbranched hydrocarbon chain having from 1 to 15 carbons and linked to oxygens. Non-limiting examples include methoxy, ethoxy and the like.

The term "ProC3G™" (commercially available ChromaDex®, Inc. Irvine, Calif. product) means a cyanidin 3-glucoside anthocyanin extracted from black rice and containing approximately 28% cyanidin 3-glucoside by weight with an additional 5% other anthocyanins.

The term "medicament" as used herein refers to any wound treatment, including but not limited to the group consisting of burn relief medications, anesthetic agents, wound cleansers, antiseptic agents, scar reducing agents, immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents, inhibitors of prostaglandin synthesis, antioxidants, and mixtures thereof.

Unless stated to the contrary, a formula with chemical bonds shown only as solid lines and not as wedges or dashed lines contemplates each possible isomer.

The term "nutraceutical" as used herein refers to any food stuff, including a dietary supplement or fortified food, provided for potential health and medical benefits.

Reference will now be made in detail to specific aspects of the disclosed materials, compounds, compositions, and methods, examples of which are illustrated in the following description and examples, and in the figures and their descriptions.

The present invention provides methods, compositions and uses for treating and promoting healing of a wound. More specifically, the methods and compositions described herein include the administration of an anthocyanin or an anthocyanidin or metabolites thereof, preferably PCA and 2,4,6 Trihydroxybenzaldehyde (2,4,6 THBA) for promoting wound healing by reducing or preventing microbial growth and inducing the activation and or optimization of growth hormones.

The methods and compositions are used for the treatment of mammals, including humans. As with humans, there is a need for new antimicrobial compositions for the treatment of animals, including equine, canine and feline, due to resistance or allergic reactions to current antimicrobial compositions or agents. Therefore, the methods and compositions disclosed herein will be useful for the treatment and promotion of wound healing in livestock as well as domestic pets and will have broad-spectrum activity against microbes.

The present invention provides a broad spectrum antibiotic. The inventor has shown the PCA and 2,4,6 Trihydroxybenzaldehyde (2,4,6 THBA) are a broad spectrum antibiotic. The inventor has shown that the parent anthocyanins or an anthocyanidins had limited antibiotic properties including cyanidin chloride. Further the subsequent acids in the metabolic chain; vanillic and hippuric acid had little activity as well. The inventor has thus identified the specific metabolites in the chain that had the antibiotic properties.

Methods and compositions described herein include the administration of an anthocyanin or an anthocyanidin or metabolites thereof, preferably PCA and 2,4,6 Trihydroxybenzaldehyde (2,4,6 THBA) as a skin sterilizer (antiseptic). The normal human skin bacterial resident flora is one source of surgical site infections. There are several available topical application means of decreasing the bacterial presence prior to surgery. Two such commercially available preparations are Chloroprep® and Betadine®. Reports of their effectiveness in the medical literature show residual bacteria. *Propionibacterium acnes* is one such organism.

Figure 32:
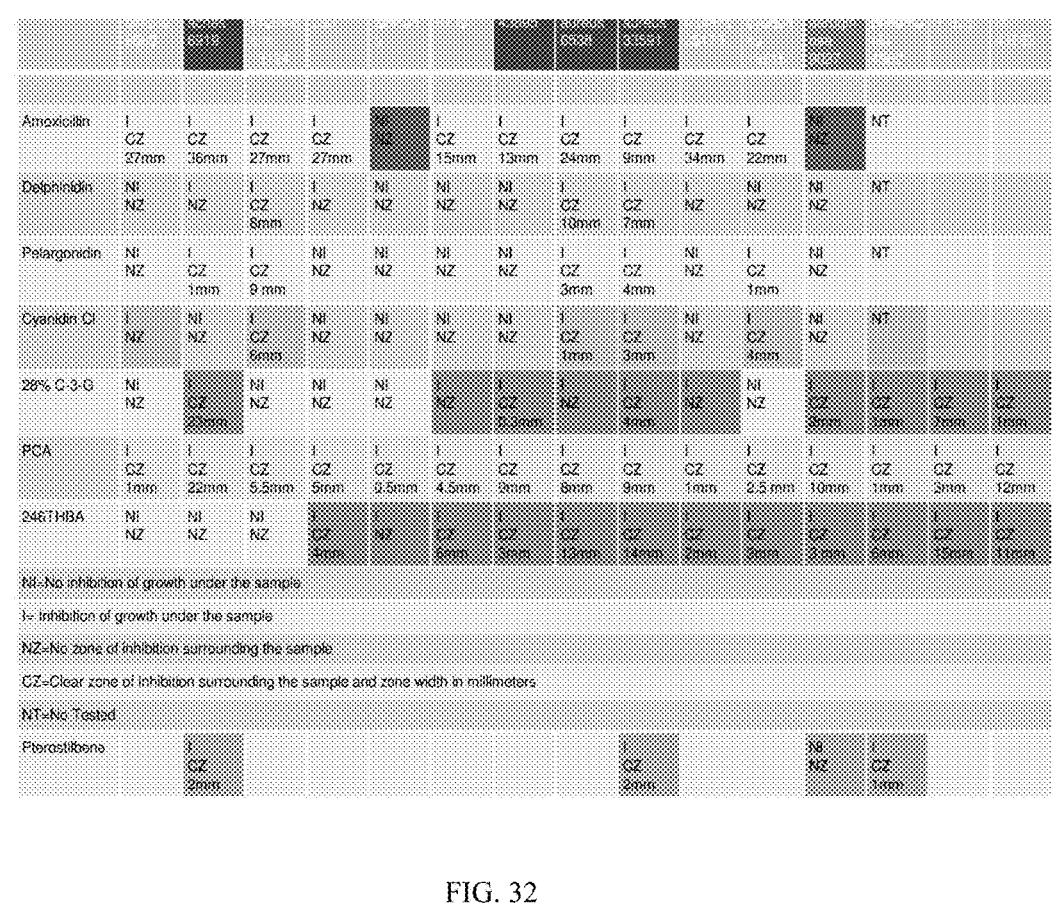

Therefore there is a need for a more effective means of pre-operative human skin treatment. Protocatechuic acid (PCA), a phytochemical metabolite, may be one such chemical reagent. We have shown its broad spectrum anti biotic properties in vitro. In addition, in vivo testing in animals has demonstrated its bactericidal properties on taped stripped open skin wounds. Therefore it was reasonable to study its potential application as a skin antiseptic. For example, a composition of PCA and 2,4,6 Trihydroxybenzaldehyde (246 THBA) or mixtures thereof can be applied to the skin or wound in advance or after a surgical or dental procedure to kill bacterial present on the skin or wound. It has been shown (See FIGS. 6 and 32) that PCA and 2,4,6 THBA have the ability to kill a wide spectrum of microbes. For example, FIG. 6 provides the results of testing showing that protocatechuic acid (PCA), the main metabolite from anthocyanins and anthocyanidins, was effective against all bacteria tested as well as *C. albicans* and *K. pneumonia*. Importantly for skin wound treatment, PCA was effective against *S. aureus* 6538 and 33591 (MRSA) and *P. aeruginosa*. PCA was also effective on *C. albicans*, which is important considering its ability to form biofilms and difficulty in treating *C. albicans* when existing with a catheter or implant. In FIG. 32, it is shown that PCA is effective against *C. difficile, P. acnes* 6919, *E. coli* 8739 and 43895, *S. Aureus* 6538, *S. Aureus* 33591, *P. Aeruginosa* 9027, methicillin resistant *staphylococcus epidermis* (MRSE), including MRSE ATCC 51625, and *Legionella* 43662, and others. FIG. 32 shows that 2, 4, 6 THBA is effective against *E. coli* 8739 and 43895, *S. Aureus* 6538, *S. Aureus* 33591, *P. Aeruginosa* 9027, methicillin resistant *staphylococcus epidermis* (MRSE), including MRSE ATCC 51625, and *Legionella* 43662, and others. In addition, by treating the skin, the compositions promote wound healing by reducing or preventing microbial growth and inducing the activation and or optimization of local skin growth hormones.

The present invention also provides methods, compositions and uses for treating surfaces (solid, smooth, porous or semi-porous, or cloth-like) and liquids to reduce microbial growth or to sanitize or sterilize the surface. More specifically, the methods and compositions described herein include contacting any surface with a composition comprising an anthocyanin or an anthocyanidin or metabolites thereof (preferably PCA and 2,4,6 Trihydroxybenzaldehyde (2,4,6 THBA)) thereby reducing or preventing microbial growth on said surface, or to sanitize or sterilize the surface. The surfaces can be in the health care setting, sports setting or even food preparation settings or any setting where sterile surfaces are required.

The compositions can be applied to solid surfaces such as implants, or solid surfaces like operating tables, benches, equipment, patient beds, etc. or surgical instruments to sanitize or sterilize the surface. For example, in the case of implants, the implants can be treated and coated with the compositions before inserted into the patient. Likewise, the instruments may be treated before use on a patient. Solid surfaces such as operating tables, other equipment and other surfaces can be treated as well by spraying of the surface with compositions comprising PCA, 2,4,6 THBA or mixtures thereof.

In addition, the compositions can be applied to smooth, porous or semi-porous, or cloth-like surfaces such as wound dressings, bedding, vascular implants, bandages, etc. The material can be treated with the PCA solution and then used immediately or the material can be allowed to dry and then used. For example, a bandage can be treated with PCA and then allowed to dry and store (for about up to 2 years known shelf life). When needed, depending upon the nature of the wound, the bandage can either be applied directly to the wound or can be wetted with water, 70-90% isopropyl alcohol, saline or propylene glycol and/or essential oils and then applied to the wound. It is preferred to use propylene glycol and an essential oil as they enhance the absorption of PCA into the skin.

When the antimicrobial composition of this invention is applied to as an element of a covering or bandage, to adhere to a surface to be treated, such as a wound, the antimicrobial composition generally can include a concentration of the PCA or 246 THBA or mixtures thereof of at least 1.24% and 30% by weight of the compound depending upon the chemical nature of the vehicle, the target being treated and the species of bacteria to be treated. In certain embodiments a 25 mM concentration of PCA is applied to the bandage. In Trans Pharm's independent laboratory experiment 367 on tape stripped wounds or rodents, the data demonstrated that C-3-G at 100 and 200 mM significantly decreased the bacterial burden of *P. aeruginosa* in skin tissue at 48 and 96 hours. The treatment with 25 mM PCA significantly decreased the bacterial burden of *P. aeruginosa* at the 48 hour interval.

Further, the isolated anthocyanins, anthocyanidins, or metabolites compounds this invention will be between 20-30% by weight of the compound for one intended use and more preferably, between 1.24% and 30% by weight of the compound depending upon the chemical nature of the vehicle, the target being treated and the species of bacteria to be treated. Preferably the antimicrobial composition comprises PCA or 2, 4, 6 Trihydroxybenzaldehyde (2,4,6 THBA) or mixtures thereof. These bandages can promote wound healing not only as they are effective against killing microbes, but they also promote healing by inducing the activation and or optimization of local skin growth hormones.

Further, the methods and compositions described herein include adding the composition comprising an anthocyanin or an anthocyanidin or metabolites thereof to liquid or fluid, including other sanitizing solutions and/or sanitizing components, thereby reducing or preventing microbial growth on said surface. Further still, the methods and compositions described herein include adding the composition comprising an anthocyanin or an anthocyanidin or metabolites thereof to any other vehicle, including but not limited to a powder, paste, cream foam, gel, wipes, other sanitizing components and the like thereby reducing or preventing microbial growth on said surface.

Included in the invention are compositions for, and methods of destroying, killing or significantly reducing a bacterial biofilms. Biofilms are comprised of bacteria that form colonies and produce a surrounding matrix film to protect themselves. The biofilm forming bacteria can form colonies that attach to foreign bodies, each other and tissues. The bacteria aggregate in clusters and are surrounded by extracellular polymer matrix. The biofilms are hard to destroy and therefore kill the underlying bacteria and provide the basis for much of the antibiotic resistance that has developed. Biofilms can be found attached to surfaces such as implants and catheters and they also can be embedded in the biological host, such as for example cystic fibrosis wounds. MRSA biofilms play a role in many device-related infections such as native valve endocarditis, otitis media, urinary tract infections, cystic fibrosis, acute septic arthritis, total joint implantation, catheters, pacemakers, etc. The formation of a biofilm is a two-step process: 1. Adherence of cells to a foreign body surface; and 2. Accumulation of cells to form multilayered cell clusters. A trademark of biofilm formation in staphylococci is the production of polysaccharide intercellular adhesion.

The present invention thus provides a composition that destroys biofilms. The composition is preferably PCA. The PCA may be mixed with 70% isopropyl alcohol and or small amount of essential oil; i.e. lemon, peppermint, etc. The concentration of PCA can be anywhere from about 20% by weight PCA to 100% PCA. Preferably the concentration of PCA varies with the intended purpose from 1.24%, 20%, 30%, 20-50% or 20-40% or 20-30% by weight. When the PCA is used in a crystal form, then the crystals can be up to 100% PCA by weight. The PCA may be in the form of crystals that are embedded into a material such as a cloth or a mesh, such as titanium or stainless steel. The crystals are applied to the metal where there is surface configuration that provides for housing of the crystal on the surface. The same is for cloth material that has mesh or surface to house the physical crystals by size. The may be seen in vascular grafts. They remain in place in crystal form until activated when subject to fluid common to the mammalian body.

The inventor has shown that a composition comprising PCA was able to stop the formation of a biofilm as well as kill bacterial in already formed biofilms. The biofilms tested were *Pseudomonas Aeruginosa* ATCC 700888 and *Staphylococcus aureus* ATCC 33591 (MRSA). The tests are described in more details below and in Examples 7 and 8.

It should be noted that the dose of the parent anthocyanin, anthocyanidin, and or the main metabolites, PCA and or 246 THBA vary with the application and the vehicle. For instance the dose used on an open rodent taped stripped skin would be conditioned by the wound's tolerance of the vehicle which in this case would be water, normal saline or like. The amount of PCA for instance that can be dissolved in water is 1.24 grams per 100 ml. In the rodent the effective dose of C-3-G and PCA were expressed in millimolar (mM) as 25 to 200 mM dose. Conversion factors are necessary to make comparisons to larger doses used in other applications. 78 mM (mmole/L) PCA would be 12.021 g PCA per Liter. Therefore 25 mM/L would be 3.852 grams per liter or 0.0038 mg/ml. The fluid applied was 100 mL or 0.1 milliliter. Therefore, for example, the dose of PCA that was bactericidal on *Pseudomonas aeruginosa* on taped stripped rodent skin was 0.00038 grams. When treating intact normal human skin as in the Loma Linda Medical School testing, it was shown the 1.24 gram in 100 ml of water would only decrease the number of colonies of *Propionibacterium acnes*. Note that there was no skin penetration properties to water by this method. The increase of PCA concentration was possible to as much as 17% when in composition of matter was 70% isopropyl alcohol with propylene glycol and essences of peppermint oil. This composition had skin penetration properties. However the amount of liquid applied was no more than one milliliter by cotton swab. Therefore the topical dose on intact human skin was 1.7 grams (estimated). This is many times that required for traumatized taped stripped skin.

The amount of PCA necessary for coating metal and or cloth was 20 to 30% PCA or 20-30 grams per 100 ml of 70% isopropyl alcohol. These compositions allowed for higher concentrations, and also evaporated rapidly to dry state of PCA crystals on the metal or cloth.

The next variable was the species of bacterial to be eradicated. It was noted that a 10% concentration of PCA was not effective on *Pseudomonas aeruginosa*. See FIG. 33. However a 20% concentration was effective. See FIG. 34.

The biofilms destroying properties of coating metal and linen for Methicillin resistant *Staphylococcus aureus* required higher dose than *Pseudomonas aeruginosa*. See FIG. 35. However at concentration of 30%, it was effective. See FIG. 36. The application on an implant allowed to dry had the above results. However, when a glass surface is covered with 10 million biofilms colonies the results differ with the concentration and the bacteria biofilms to be eradicated. The glass surface experiments are described in example 8. Generally, Glass slides were inoculated at Time 0. Batch phase was performed for 6 hours to allow for biofilm formation on the glass slides. The drip flow mechanism was then turned on to provide a continuous flow of nutrients to the glass slides over 48 Hours. After 48 hours, 2 sets of glass slides were sprayed with a 30% PCA solution. One set was removed and analyzed for biofilm reduction after 30 minutes. The other set was removed after 60 minutes. 2 sets of control slides were also removed and analyzed after 30 minutes and 60 minutes. The control slides were not treated with 30% PCA and were used for comparative purposes. The Log Reduction Calculations were performed as follows: The mean 30% PCA treated samples were compared to the mean positive control samples, per time point evaluated. The results were as follows for a single spray of 30% PCA in isopropyl alcohol on 10 million biofilms colonies of *Pseudomonas aeruginosa*. See FIG. 40. The concentration of 30% has lesser effect on MRSA, but still 90%. See FIG. 41. These experimental concentrations of biofilms covered pathogens that far exceed the concentrations and numbers found in practice.

The above experimental results show discovery of dose and composition requirements for any given intended use related to nature of the wound, the disinfectant intentions, environmental conditions of coating and or spraying plus consideration of the bacterial species and biofilms to be destroyed.

Regarding wound healing and the treatment of wounds comprising the anthocyanins and anthocyanidins and their metabolites using compositions of the present invention, these compositions also have broad spectrum activity against a wide range of microbes. These compositions, however, may also be used in combination with other wound treatments, including other antimicrobials. In certain embodiments, the additional antimicrobial is not sulfamethoxazole.

Figure 8A:
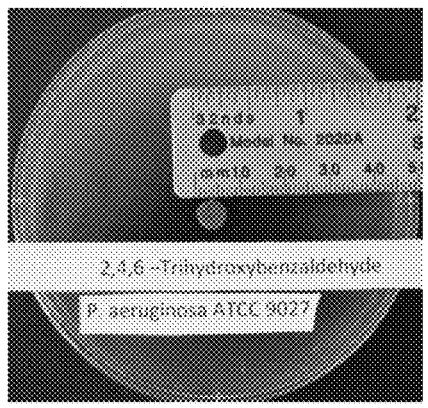
FIG. 8A is a photographic image illustrating in vitro test results of 2, 4, 6 Trihydroxybenzaldehyde against *P. aeruginosa.
Figure 8B:
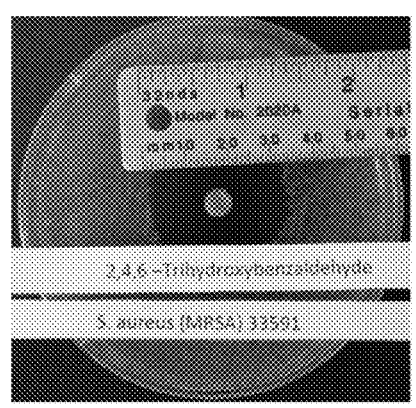
* FIG. 8B is a photographic image illustrating in vitro test results of 2, 4, 6 Trihydroxybenzaldehyde against *S. aureus* 33591 (MRSA).
Figure 8C:
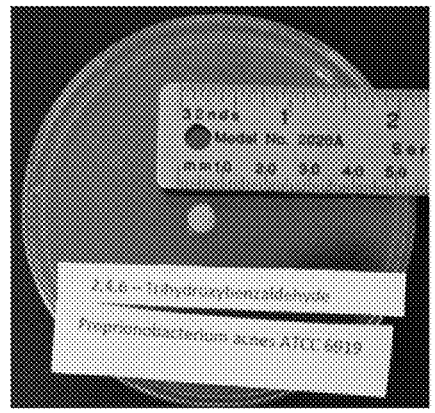
FIG. 8C is a photographic image illustrating in vitro test results of 2, 4, 6 Trihydroxybenzaldehyde against *P. acnes.*

The identification of anthocyanins and anthocyanidins or combinations of anthocyanins, anthocyanidins or their metabolites that are bactericidal or antimicrobial was determined by conducting in vitro testing. Anthocyanidins that were tested at 100 mM (44.938 grams per liter) with less than one milliliter per dose included delphenindin, pelargonindin, and cyanidin CI and cyanidin-3-glucoside. Protocatechuic acid and 2, 4, 6 trihydroxybenzaldehyde, the anthocyanidin metabolites, were also tested at the same concentrations. Referring to FIGS. 6-8, delphinidin limited growth against C. perfringens, S. aureus, and MRSA. Pelargonidin limited growth of P. acnes, C. perfingens, S. aureus, MRSA, and S. pyogenes. Cyanidin CI was effective against C. difficile, C prefringens, S. aureus ATCH 6538, S. aureus (MRSA) ATCH 33591, S. mutans, and S. pyogenes. C3G (approximately 28% by weight) had limited effectiveness during this study (18-24 hours for aerobes; 48 hours for anaerobes (C. albacans and L. casei). This proprietary C3G formulation, however, was effective against P. acnes, E. coli, MRSA, K. pneumoniae and P. aeruginosa. Protocathechuic acid (PCA), the main metabolite from anthocyanins and anthocyanidines, was effective against all bacteria tested as well as C. albicans and K. pneumonia. Importantly for skin wound treatment, PCA was effective against S. aureus 6538 and 33591 (MRSA) and P. aeruginosa. PCA was also effective on C. albicans, which is important considering its ability to form biofilms and difficulty in treating C. albicans when existing with a catheter or implant. 2, 4, 6 Trihydroxybenzaldehyde was effective against E. coli, K. pneumonia, P. aeruginosa, S. aureus 6538 and 33591 (MRSA); it also was effective against A. pullulans, ATCC 15233, a fungi.

Figure 9A:
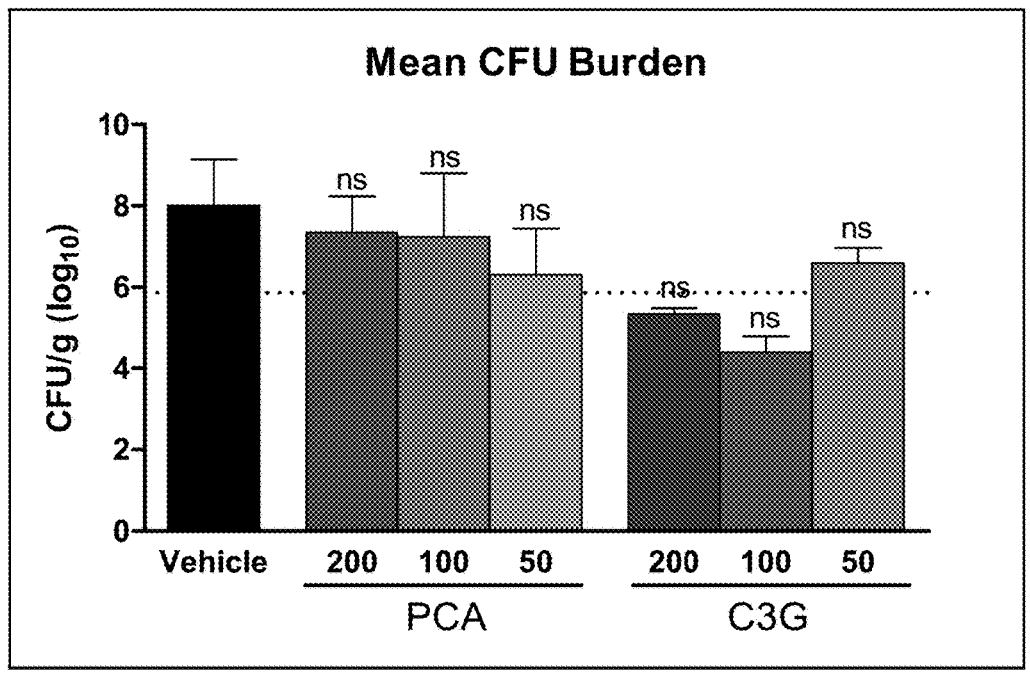
FIG. 9A shows the results of a rodent back skin tape study where concentrations of PCA and C3G in a vehicle of water were utilized to determine effectiveness against *P. aeruginosa* skin infections.
Figure 9B:
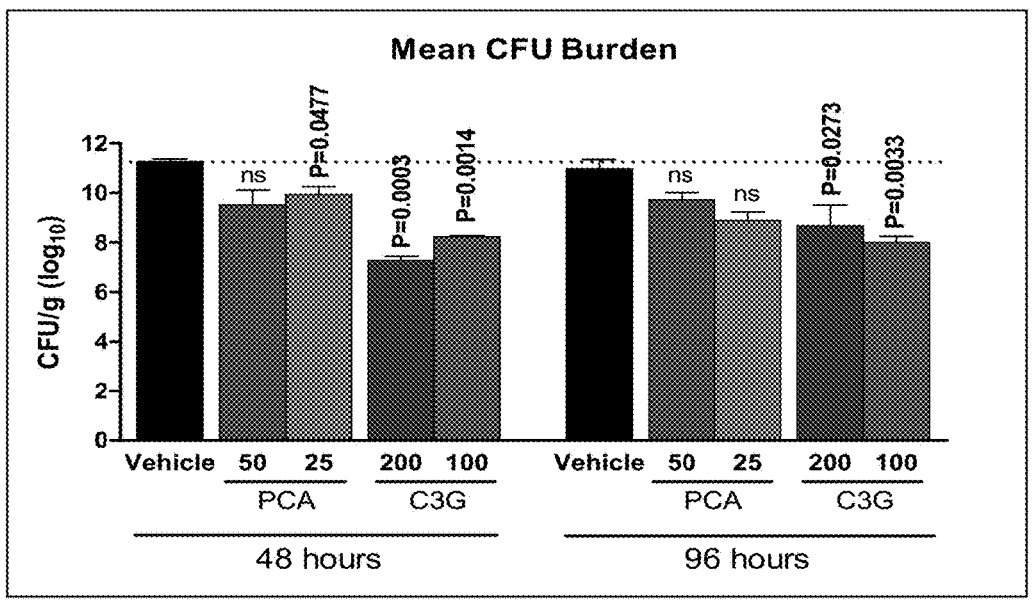
FIG. 9B shows the results of rodent back skin tape study where concentrations of PCA and C3G in a vehicle of water were utilized to determine effectiveness against *P. aeruginosa* skin infections.

While specific dosages of certain anthocyanins and anthocyanidins were determined to have the above mentioned effects against certain bacteria, in vivo testing were conducted to determine optimal dosages and to confirm the ability of a topical application of these compounds to have antimicrobial effect while prompting healing of a wound. It was hypothesized that certain dose and interval topical application of a water soluble solution of PCA and/or C3G (28% of C3G by weight) at certain concentrations based upon molecular weight would kill or reduce the bioburden of Pseudomonas aeruginosa while healing the wound as evidence by optimization of the local growth hormones and confirmed by histological evidence. Referring to FIG. 9, a decrease in bacterial burden in the skin at 96 hours days was noted (CFU means colony forming units). A concentration of 50 mM of PCA was found to be most effective; higher concentrations of PCA were not as effective at decreasing bacterial burdens. The most effective concentration of C3G was 100 mM. Importantly, histological evaluations of skin samples from the study confirmed healing at 48 and 96 hours with proliferation of parafollicular cells and migration to cover the skin surface. There was minimal inflammation in the dermis. There was collagen proliferation in the dermis. In this application, in some embodiments, anthocyanins or anthocyanidins and metabolites thereof are provided in concentrations of about 10 to 200 mM. In other embodiments, anthocyanins, or anthocyanidins, or metabolites thereof are provided in any recited composition or method of use in a range of between 20 to 200 mM. In yet other embodiments, the anthocyanin, anthocyanidin, or metabolites thereof provided in any recited composition or method of use is provided in a range of between 20 to 100 mM. In yet other embodiments, the anthocyanin, anthocyanidin, or metabolites thereof provided in any recited composition or method of use is provided in a range of between 20 to 50 mM. In a preferred embodiment, anthocyanins or anthocyanidins and or their metabolites are provided in concentrations of about 100 mM or less.

As provided in FIG. 1, bacteria have a range of pH at which growth is optimized, and most bacteria are more viable at basic pH ranges. Generally, anthocyanins, anthocyanidins and their metabolites also have an acidic pH and have the potential to have bactericidal or bacteriostatic modes of action. Because C3G and PCA reagents have an acidic pH, their bactericidal or bacteriostatic mode of action is by direct contact with the bacteria.

Anthocyanins and anthocyanidins were further studied to determine effects on wound healing, including whether they had any effect on the optimization of local growth hormone activity at the wound site along with other supporting histological evidence of promoting healing.

Local growth hormones are important substances in the control of wound healing. Equally as important, however, is to optimize the amount of these hormones desirable for promoting wound healing while avoiding scar formation and keloids.

Examples of common local growth hormones related to skin wound healing include Epidermal growth factor (EGF), Insulin-like growth factor-1 (IGF-1) and Transforming Growth Factor-Beta (TGF-β). Epidermal growth factor or EGF is a growth factor that stimulates cell growth, proliferation, and differentiation by binding to its receptor EGFR. IGF-1 is important in skin repair by stimulating keratinocyte proliferation and migration as well as collagen production by fibroblasts. Its expression is important during wound healing such that retarded healing has been correlated with reduced IGF-1 levels. While local administration of IGF-1 to wound sites enhanced wound closure and stimulated granulation tissue formation, increased IGF-1 receptor expression was reported in chronic wounds and in hypertrophic scars. Additionally, IGF-1 stimulation was associated with increased invasive capacity of keloid fibroblasts. Systemic delivery of IGF-1 also caused hyperglycemia, electrolyte imbalance, and edema. Therefore it is desirable to have slightly elevated but not over elevated IGF-1 by a treatment modality. TGF-β also is important in skin would healing; however, it is considered a pro-fibrotic growth factor and increased levels of TGF-β or prolonged presence has been identified as causing hypertrophic scaring.

Figure 11A:
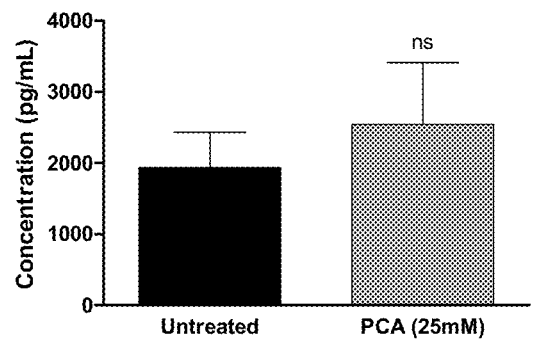
FIG. 11A shows the results of a rodent back skin study to determine the effects of PCA and C3G on the local growth hormones in untreated skin wounds of rodents. A concentration of 25 mM PCA increased local growth hormone levels of IGF-1 at the site of the untreated skin wound. FIG.
Figure 11B:
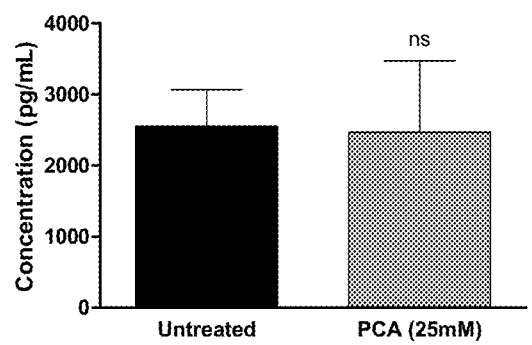
FIG. 11C shows the results of a rodent back skin study to determine the effects of PCA and C3G on the local growth hormones in untreated skin wounds of rodents. A concentration of 25 mM PCA increased local growth hormone levels of EGF at the site of the untreated skin wound.
Figure 11C:
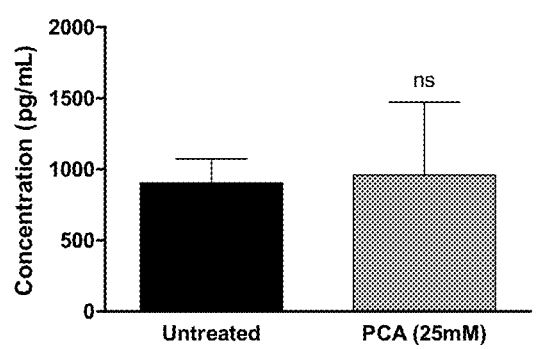
Figure 12:
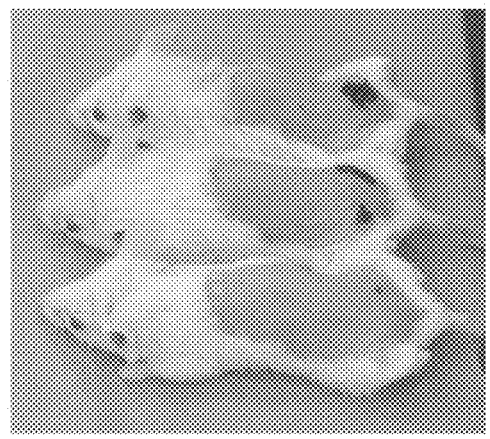
FIG. 12A is a photographic image of rodents treated with a topical solution of C3G (28%); at an acidic pH, this solution maintains a purple or red color and quickly metabolized at elevated pH levels, the C3G changes to a pink or even clear color. In mouse model experiments, however, as observed in the image, the purple color of C3G remained on the rodent wound surface scar, thus indicating the pH remained acidic on the wound surface. The C3G material on the surface was confirmed by subsequent histology.
FIG. 12B is a photographic image of tissue from a study utilizing the homogenized wound tissue method used in this study, whereby the purple color indicates that the wound probably retained an acidic pH.
Figure 12:
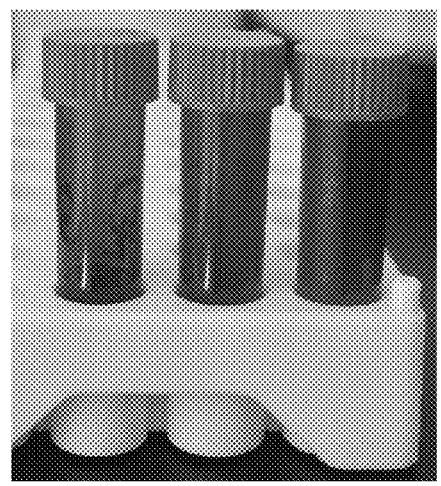
Figure 13A:
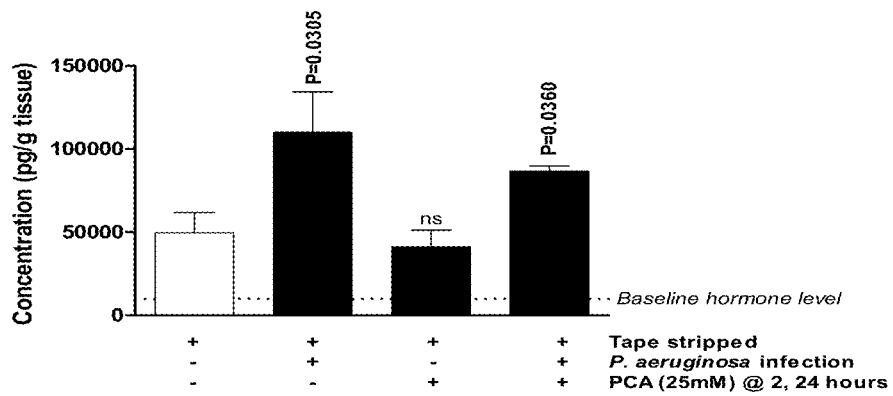
FIG. 13A shows the IGF-1 response to 25 mM PCA in various environments, including tape stripped, tape stripped and infected with *P. aeruginosa*, tape stripped and treated with PCA, and tape stripped infected with *P. aeruginosa*, and PCA treated.
Figure 13B:
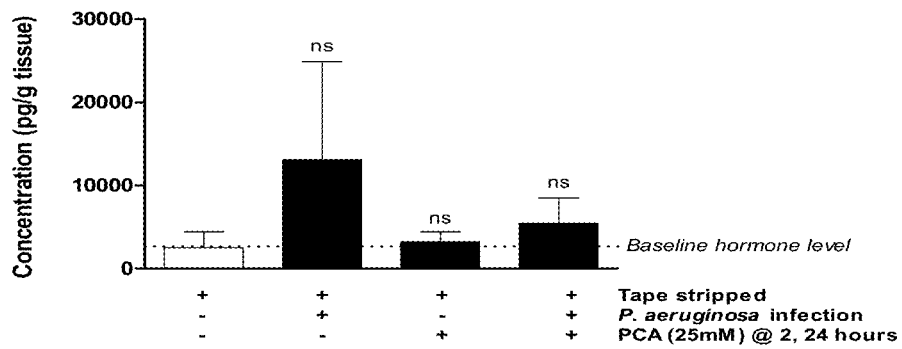
FIG. 13B shows the TGF-β response to 25 mM PCA in various environments, including tape stripped, tape stripped and infected with *P. aeruginosa*, tape stripped and treated with PCA, and tape stripped infected with *P. aeruginosa*, and PCA treated.
Figure 13C:
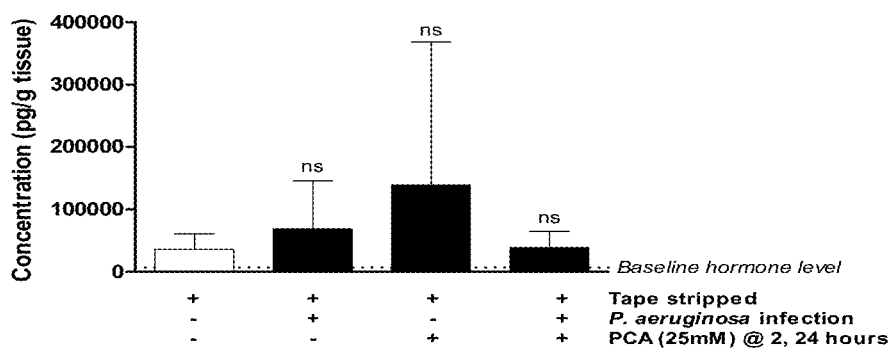
FIG. 13C shows the EGF response to 25 mM PCA in various environments, including tape stripped, tape stripped and infected with *P. aeruginosa*, tape stripped and treated with PCA, and tape stripped infected with *P. aeruginosa*, and PCA treated.

Referring to FIGS. 11-13, tests were performed on rodent skin to explore the effects of PCA on the local growth hormones in rodent skin. A concentration of 25 mM PCA increased local growth hormone levels at the site of the untreated skin wound. In particular, FIG. 11 demonstrates that a single reagent or compound would optimize local growth hormones to promote healing without scarring. Approximately 25 mM PCA was the optimal reagent and dose. As demonstrated in FIG. 13, optimization is possible using the compositions of the present invention. In FIG. 13, all three local growth hormones were lowered in the simulated clinical pathological environment (stripped and infected); however, the lowering of these hormones was not to the extent of absences. Hence, the necessary IGF-1 is still above the controls in this environment; however, the scar forming properties of the other two hormones have been markedly reduced. Therefore, optimization of local growth hormones is achieved. In FIG. 13, the optional concentration of PCA was confirmed as 25 mM PCA in this situation and environment, meaning local growth hormone growth levels were optimized at this dosage such that IGF-1 as moderately elevated while TGF-β and EGF levels were decreased. This is important to promote wound healing while preventing potential scarring.

The therapeutic effective dose may vary depending on a wide variety of factors. For instance, the dose may vary depending on the formulation, method of application of the therapeutic reagent or combination with other reagents, or compositions, compounds or combination of compositions or compounds to the wound.

Methods (General)

According to one aspect of this invention, there is provided an antimicrobial composition and a method of promoting wound healing by reducing microbial growth. A method of promoting healing of a wound in a mammal is provided, comprising administering an anthocyanin or an anthocyanidin to the mammal in need of such treatment a therapeutically effective amount of the anthocyanin or anthocyanidin compound wherein microbial growth is prevented or reduced and local growth hormone activity is optimized.

In a further embodiment, a method of promoting healing of a wound in a mammal is provided; comprising administering an anthocyanin metabolite or an anthocyanidin metabolite to the mammal in need of such treatment a therapeutically effective amount of the metabolite or an anthocyanidin metabolite compound wherein microbial growth is reduced and local growth hormone activity is optimized.

In some embodiments, a method of promoting healing a wound further comprises applying a wound dressing or bandage that has been treated with a composition of PCA or 246 THBA or mixtures thereof.

In yet another aspect of the present invention, a method of treating *P. acnes* in a patient in need thereof is provided, comprising administering an anthocyanin metabolite to the patient in need of treatment in an therapeutically effective amount of protocatechuic acid wherein growth of *P. acnes* is reduced. FIG. 32 shows that both C-3-G and PCA were able to kill *P. acnes*, specifically *P. acnes* 6919.

In another aspect of the present invention, a method of prophylactically treating a preoperative skin incision site is provided, comprising administering an anthocyanin, an anthocyanidin and/or a metabolite to a patient in need of such treatment an effective amount of the anthocyanin or anthocyanidin compound wherein microbial growth is prevented or reduced.

In another aspect of the present invention, a method of disinfecting a surface comprising contacting said surface with an anthocyanin, an anthocyanidin and/or a metabolite thereof in an effective amount of the anthocyanin, anthocyanidin and/or metabolite compound wherein microbial growth is prevented, reduced or eliminated and, further, where the microbial growth that is reduced is methicillin resistant *staphylococcus aureus* (MRSA).

In another aspect of the present invention, a method of disinfecting or sterilizing a surface is provided comprising contacting said surface with an anthocyanin, an anthocyanidin and/or a metabolite thereof or combination thereof in an effective amount of the anthocyanin, anthocyanidin and/ or metabolite or combination thereof wherein microbial growth is prevented, reduced or eliminated and, further, where the microbial growth that is reduced may be an endogenous or exogenous source, including but not limited to *P. acnes, S. aureus, P. aeruginosa, E. coli, S. epidermidis, S. pneumonia, Streptococcus species, C. difficile* and *Legionella*.

In another aspect of the present invention, a method of post-operative treating a post-operative skin site is provided, comprising administering an anthocyanin, an anthocyanidin and/or a metabolite to a post-operative skin site, such as a skin graft, skin graft donor site, a microdermabrasion site, or a surgical incision site, in an effective amount of the anthocyanin, anthocyanidin and/or metabolite compound wherein microbial growth is prevented, reduced or eliminated and local growth hormone production is optimized.

This disclosure also provides for a method comprising contacting a surface with an effective amount of the antimicrobial composition. By the term "effective amount" of a composition as provided herein is meant an amount of a composition sufficient to provide the desired benefit, either bactericidal or bacteriostatic (e.g., reduction or prevention of microorganism growth or survival). As disclosed herein, the exact amount required will vary from use to use depending on a variety of processing parameters, as understood by one of ordinary skill, such as the type of surface, the type of microorganism to be treated, the surface size, the mode of deliver (e.g., aerosol, spraying or dipping), and the like. Determination of what constitutes an "effective amount" is made by routine testing with known concentrations and adjusting those concentrations as needed to obtain the desired benefit and can be determined by one of ordinary skill in the art using only routine experimentation.

When the antimicrobial composition of this invention is applied to a surface to be treated, the antimicrobial composition generally can include a concentration of the anthocyanins and anthocyanidins of at least 25 mM concentration, not including the carrier. Further, the isolated anthocyanins, anthocyanidins, or metabolites compounds this invention will be between 90%-97% by weight of the compound, and more preferably, between 95%-98% by weight of the compound.

When the antimicrobial composition or compositions of this invention are applied to a surface to be treated may be diluted for use as a sanitizer or as a preventive or prophylactically, and at greater concentrations for treatment.

In another aspect of the invention provides a method of inhibiting growth of a biofilm on a solid, smooth, porous or semi-porous, or cloth-like surface (such as but not limited to a cloth, wound dressing, bandage, heart or vessel grafts) by treating the surface with a composition of the present invention, preferably comprising PCA. The surface can be any solid, smooth, porous or semi-porous, or cloth-like surface, including implants that are inserted into a patient.

Compositions

Disclosed herein, in one aspect, are antimicrobial compositions. The disclosed antimicrobial reagents and compositions can be used to eliminate, reduce, and/or prevent microorganism growth, viability, or survival.

The present invention thus provides a composition that destroys or inhibits growth of a biofilm. The composition is preferably PCA. The PCA may be mixed with 70% isopropyl alcohol. The concentration of PCA can be anywhere from about 20% PCA to 100% PCA. Preferably the concentration of PCA is about 20-50% by weight, or is about 20-40% by weight or is about 20-30% by weight or is 30% to 50% by weight. Additionally, the PCA may be in the form of crystals that are embedded into a material such as a cloth or a mesh, such as titanium or stainless steel.

For compositions applied to the skin or a bandage the PCA crystals need to be dissolved in a liquid. The inventor found that PCA in water only decreased the colonies of P. acnes in and on human skin as the PCA concentration he was able to achieve when dissolving in water was limited to 1.24%. The inventor had to increase the concentration of PCA above 1.24% and to do this, the inventor discovered that he would have to use isopropyl alcohol instead of water to dissolve the crystals. The use of isopropyl alcohol in the combination was not an obvious choice because isopropyl alcohol alone only is marginally effective in killing bacteria. So even after using isopropyl alcohol to dissolve the PCA, the inventor discovered that even at 10% PCA in isopropyl alcohol, the composition was only marginally effective. So the inventor discovered that he had to increase the PCA to at least 17% in isopropyl alcohol plus add two skin penetration vehicles (propylene glycol and essential oil) to achieve the desired and most effective means of controlling P. acnes, which are deep in the skin. Accordingly, the invention provides a composition comprising about 17 to 40%, or 17 to 30% or 17 to 20% by weight of PCA, isopropyl alcohol, propylene glycol and an essential oil, preferably of peppermint, or a citrus fruit (i.e. lemon, grapefruit, orange, lime, etc.). This composition is useful in the methods described in the invention, for example as a skin antiseptic as a surface disinfectant, as a spray to disinfect a surface, etc. Further, the inventor found that neither propylene glycol or essential oil alone or in combination absent the isopropyl alcohol provide enough concentration of PCA to be above the effective range of 10% concentration. Therefore the composition of the invention, to be effective should have at least PCA at 17+% by weight in at least 70-90% isopropyl alcohol, propylene glycol (15 mls in a 105 ml total solution) and the essential oil; i.e. peppermint or lemon etc.

The invention further provides a composition of PCA wherein the composition comprises or consists of PCA that can be applied directly or provided in various vehicles depending upon the application. PCA of 1.24 grams in 100 milliliters of water was effective on open wound. A composition of 70% isopropyl alcohol, propylene glycol and essential peppermint oil was also effective in use as a skin antiseptic, especially against P. acnes. Studies showed that higher concentration of 10% PCA (20 grams in 90 milliliters of 70% isopropyl alcohol) was more effective than PCA in water. However the following concentration was more effect than just PCA in isopropyl alcohol—the composition consisted of PCA (20 grams) 70% isopropyl alcohol (85 ML), propylene glycol (15 ml) and an essential oil (5 ml).

The invention also provides bandages, wound dressings and the like comprising PCA or 246 THBA.

In some embodiments and aspects, the disclosed antimicrobial composition can be selected from the list of anthocyanins, anthocyanidins, metabolites of anthocyanin and anthocyanidin metabolites, or a combination thereof. By way of example, the anthocyanin can be selected from cyanidin-3-glucoside or delphinidin-3-glucoside, cyanidin-3-galactoside, and pelargonidin-3-galactoside. Also by way of example, the anthocyanidins can be selected from cyanidin, delphinidin, pelargonidin, malvidin and petunidin. By way of example, metabolites can be selected from protocatechuic acid, 2, 3, 4 trihydroxybenzaldehyde.

In one aspect, the present invention provides for a pharmaceutical composition for promoting wound healing, comprising phytochemicals: a) an anthocyanin; or b) anthocyanidin or their metabolites such as C3G, PCA, 246 THBA, vanillic and hippuric acid. By way of example, the anthocyanin can be selected from cyanidin-3-glucoside or delphinidin-3-glucoside, cyanidin-3-galactoside, and pelargonidin-3-galactoside. Also by way of example, the anthocyanidins can be selected from cyanidin, delphinidin, pelargonidin, malvidin and petunidin. Preferably the present composition comprises PCA and 2,4,6 Trihydroxybenzaldehyde (2,4,6 THBA).

In one aspect, for example, the present disclosure provides for a pharmaceutical composition comprising protocatechuic acid (PCA) whereby said composition reduces the growth of certain microbes, including P. acnes.

In one aspect, for example, the present disclosure provides for a pharmaceutical composition comprising cyanidin-3-glucoside whereby said composition reduces the growth of certain microbes, including H. pylori.

In one aspect, the present invention provides for a pharmaceutical composition for treating a wound, comprising: a) an anthocyanin; b) anthocyanidin; or c) a metabolite of an anthocyanin or anthocyanidin in an effective amount whereby microbial growth is reduced. Preferably the present composition comprises PCA and 2,4,6 Trihydroxybenzaldehyde (2,4,6 THBA).

By way of example, the anthocyanin can be selected from cyanidin-3-glucoside or delphinidin-3-glucoside, cyanidin-3-galactoside, and pelargonidin-3-galactoside. Also by way of example, the anthocyanidins can be selected from cyanidin, delphinidin, pelargonidin, malvidin and petunidin. By way of example, metabolites can be selected from protocatechuic acid (PCA) and 2, 3, 4 trihydroxybenzaldehyde.

In another aspect, the pharmaceutical composition of this invention to treat a wound generally can include a concentration of the anthocyanins and anthocyanidins or metabolites thereof in a concentration of at least 25 mM concentration, not including the carrier. Preferably the present composition comprises PCA and 2,4,6 Trihydroxybenzaldehyde (2,4,6 THBA).

In yet another example, the pharmaceutical composition of this invention to treat a wound can include a concentration of the anthocyanins and anthocyanidins or metabolites thereof in a concentration of between 20 mM to 200 mM concentration, not including the carrier. In yet other embodiments, the pharmaceutical composition of this invention to treat a wound can include a concentration of the anthocyanin, anthocyanidin, or metabolites thereof provided in any recited composition or method of in a range of between 20 to 100 mM, not including the carrier. In another example, the pharmaceutical composition of this invention to treat a wound can include a concentration of the anthocyanin, anthocyanidin, or metabolites thereof provided in any recited composition or method of in a range of between 20 to 500 mM, not including the carrier.

Further, in one example, in a pharmaceutical composition of this invention, PCA can be provided in a concentration approximately 50-100 mM. Additionally, in one example, pterostilebene can be provided in a concentration of approximately 35-65 mM. Further, in one example, PCA can be provided in a concentration approximately 78 mM and pterostilebene at a concentration of approximately 40.6 mM to reduce microbial growth or eliminate growth. Further, in one example, PCA and psterostilbene can be provided in a combination in concentrations provided in this disclosure. In yet another example C3G would be provided at a dosage of 131, 261 and 522 mg/kg.

In one aspect, the present invention provides for a pharmaceutical composition for treating a wound, comprising phytochemicals: a) an anthocyanin; b) anthocyanidin; c) a metabolite of an anthocyanin or anthocyanidin such as C3G, PCA, 246 THBA, vanillic and hippuric acid. Preferably the present composition comprises PCA and 2,4,6 Trihydroxybenzaldehyde (2,4,6 THBA).

The present disclosure also provides for a pharmaceutical composition comprising phytochemicals: a) an anthocyanin; b) anthocyanidin; c) a metabolite of an anthocyanin or anthocyanidin such as C3G, PCA, 246 THBA, vanillic and hippuric acid. Preferably the present composition comprises PCA and 2,4,6 Trihydroxybenzaldehyde (2,4,6 THBA).

In another aspect, the present invention provides for a pharmaceutical composition for promoting wound healing, comprising phytochemicals: a) an anthocyanin; b) anthocyanidin; c) a metabolite of an anthocyanin or anthocyanidin such as C3G, PCA, 246 THBA, vanillic and hippuric acid. By way of example, metabolites can be selected from, protocatechuic acid, 2, 4, 6 trihydroxybenzaldehyde. In yet another aspect, the present disclosure provides for a pharmaceutical composition comprising phytochemicals: a) an anthocyanin; b) anthocyanidin; c) a metabolite of an anthocyanin or anthocyanidin such as C3G, PCA, 246 THBA, vanillic and hippuric acid. By way of example, the metabolites are metabolites selected from protocatechuic acid, 2, 4, 6 trihydroxybenzaldehyde.

The present disclosure provides for pharmaceutical compositions whereby the anthocyanin, anthocyanidin, anthocyanin metabolite, anthocyanidin metabolite, anthocyanin metabolite, or metabolites thereof, are isolated reagents. Preferably the present composition comprises PCA and 2,4,6 Trihydroxybenzaldehyde (2,4,6 THBA).

The present disclosure also provides for routes of administration of the pharmaceutical compositions, including oral, injection, intravenous, topical, sublingual, buccal, inhalation, intradermal, subcutaneous, soft tissue, and cutaneous.

Oral administration of the compositions of this disclosure, including oral gavage, may include a liquid or semisolid form, tablet, pill, capsule, powder, or gel. Preferably, oral administration will be in a liquid composition. Compositions including a liquid pharmaceutically inert carrier such as water may be considered for oral administration. Other pharmaceutically compatible liquids or semisolids may also be used. The use of such liquids and semisolids is well known to those of skill in the art.

Intravenous and injection administration will be in liquid form. Other pharmaceutically compatible liquids or semisolids may also be used. The use of such liquids and semisolids is well known to those of skill in the art.

Preferably, the composition is formulated as a topical composition. More preferable, the vehicle of the topical composition delivery is in the form of a liquid, salve, soap, spray, foam, cream, emollient, gel, ointment, balm or transdermal patch.

In addition to the components and administration of said compositions disclosed above, the compositions can be in the form of an aqueous solution. The compositions disclosed herein can also be in the form of a liquid, gel, suspension, dispersion, solid, emulsion, aerosol, for example, powders, tablets, capsules, pills, liquids, suspensions, dispersions or emulsions. Also, the compositions disclosed herein can be in the form suitable for dilutions. Similarly, the compositions can be in the form of a powder, cream, paste, gel or solid that can be reconstituted.

Other components can be present in the composition, if desired. For example, the antimicrobial composition can also include at least one additive selected independently from a carrier, a diluent, an adjuvant, a solubilizing agent, a suspending agent, a filler, a surfactant, a secondary antimicrobial agent, a preservative, a viscosity modifier, a thixotropy modifier, a wetting agent, an emulsifier, or any combinations thereof. For example, the disclosed antimicrobial composition can further comprise at least one surfactant selected from a cationic surfactant, an anionic surfactant, a non-ionic surfactant, and an amphoteric surfactant. Additionally, the disclosed antimicrobial and/or pharmaceutical compositions may further comprise medicament is selected from the group consisting of burn relief medications, anesthetic agents, wound cleansers, antiseptic agents, scar reducing agents, immunostimulating agents, antiviral agents, anti keratolytic agents, anti-inflammatory agents, antifungal agents, acne treating agents, sunscreen agents, dermatological agents, antihistamine agents, antibacterial agents, bioadhesive agents, inhibitors of prostaglandin synthesis, antioxidants, and mixtures thereof.

Also, the disclosed antimicrobial compositions can optionally include one or more additives such as carriers, adjuvants, solubilizing agents, suspending agents, diluents, surfactants, other antimicrobial agents, preservatives, fillers, wetting agents, antifoaming agents, emulsifiers, and additives designed to affect the viscosity or ability of the composition to adhere to and/or penetrate the wound.

In one embodiment, the disclosed antimicrobial compositions, including the selected active components, including the anthocyanins or anthocyanidins and metabolites thereof, are without causing significant undesirable biological effects or interacting in a deleterious manner with any of the other components of the composition in which it is contained.

In one embodiment, the disclosed compositions, including the selected active components, including the anthocyanins or anthocyanidins and metabolites thereof, are provided as a nutraceutical and provided as a dietary supplement without causing significant undesirable biological effects or interacting in a deleterious manner with any of the other components of the foodstuff in which it is contained.

In one aspect, the antimicrobial composition provided herein, including anthocyanins or anthocyanidins and metabolites thereof, are used in agricultural settings, including but not limited to nurseries, commercial farming, agricultural research facilities, residential gardens and produce processing facilities, and are applied to plants and trees to inhibit, reduce or substantially eliminate microbial bioburden as well as many fungal bioburden on plants, trees, and surfaces thereof, including leaf surfaces.

In another embodiment, antiseptic compositions of the present invention are formulated for use in liquids, solutions, gels, soaps, creams, powders salves and other preparations designed for topical use as antiseptic agents, sprays, foams, antibacterial treatments, wipes and the like. In another embodiment, antiseptic compositions of the present invention are formulated as a hand antiseptic.

In yet another embodiment, antiseptic compositions of the present invention are used in industrial settings such as in water treatment facilities, including swimming pools or water treatment plants, food preparation, including but not limited to poultry and fish processing facilities or produce handling and packaging settings to inhibit, reduce or substantially eliminate microbial bioburden, as well as many fungal bioburden. In addition to adding the antiseptic composition to a water supply or water supply system, industrial equipment and surfaces may be contacted with, or soaked in, the antiseptic compositions of the present invention.

In yet another embodiment, sanitizing compositions of the present invention are formulated for use in liquids, solutions, gels, soaps, and other preparations designed for use as sanitizing agents, liquids, including sprays, foams, gels, soaps, sanitizing treatments, and the like when used as a sanitizing solution, including but not limited to, use in food processing facilities, including food-processing equipment and utensils, and on other food-contact articles.

In yet another embodiment, sanitizing compositions of the present invention use in food processing facilities, including food-processing equipment and utensils, and on other food-contact articles are formulated to include any components generally recognized as safe for use in food processing facilities, including but not limited to, aqueous solutions containing potassium, sodium or calcium hypochlorite, a solution of hydrogen peroxide, an aqueous solution containing potassium iodide, sodium lauryl sulfate, sodium-toluenesulfonchloroamide, solutions containing dodecylbenzensulfonic acid, other acceptable detergents and the like.

In one aspect, the one or more of the additives can be an agent that is acceptable when used in or on foods and beverages and which can be consumed by a mammal (e.g., human, pet, livestock, etc.) along with the selected active components, including the anthocyanins or anthocyanidins and metabolites thereof, without causing significant undesirable biological effects or interacting in a deleterious manner with any of the other components of the composition in which it is contained.

In another aspect, the compositions of the present invention, including those compositions comprising: a) an anthocyanin; or b) an anthocyanidin; or c) a metabolite of an anthocyanin metabolite; or d) a metabolite of an anthocyanidin metabolite, or e) a combination thereof, are used in food processing, packing, manufacturing, handling, preparing, treating, transporting or holding as a food additive without causing undesirable effects or interacting in a deleterious manner. By way of example, protocatechuic acid can be used as an additive in meat, including the handling and processing, without causing undesirable effects or interacting in a deleterious manner with the meat.

In yet another aspect, the compositions of the present invention, including those compositions comprising: a) an anthocyanin; or b) an anthocyanidin; or c) a metabolite of an anthocyanin metabolite; or d) a metabolite of an anthocyanidin metabolite, or e) a combination thereof, are used in food processing, including cold sterilization of food containers, including bottles, without causing undesirable effects or interacting in a deleterious manner.

In other examples, the antimicrobial compositions disclosed herein can further comprise a carrier. The term "carrier" means a compound, composition, substance, or structure that, when in combination with a compound or composition disclosed herein, facilitates preparation, administration, delivery, effectiveness, or any other feature of the compound or composition. Examples of carriers include water, isopropyl alcohol ethanol, polyols (propyleneglycol, polyethyleneglycol, glycerol, and the like), vegetable oils, and suitable mixtures thereof. "Pharmaceutically acceptable carrier" means a compound, composition, substance, or structure that is useful in neither preparing a pharmaceutical composition which is generally safe, non-toxic, and neither biologically nor otherwise undesirable and includes that which is acceptable for veterinary as well as human pharmaceutical use.

In a further example, the antimicrobial compositions disclosed herein can also comprise adjuvants such as preserving, wetting, emulsifying, suspending agents, and dispensing agents. Prevention of the action of other microorganisms can be accomplished by various antifungal agents, for example, parabens, chlorobutanol, phenol, and the like.

Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The disclosed antimicrobial compositions can also comprise solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofur fury 1 alcohol, polyethyleneglycols and fatty acid esters of sorbitan or mixtures of these substances, and the like. The additives can be present in the disclosed compositions in any amount for the individual anthocyanin or anthocyanidin compound components.

EXAMPLES

Example 1: Use of In Vitro Studies for Antimicrobial Susceptibility Testing of Anthocyanins, Anthocyanidins, or Metabolites and Compounds Thereof This example describes the method for testing the antimicrobial susceptibility of anthocyanins, anthocyanidins, or metabolites and compounds thereof. The Kirby-Bauer method of disc diffusion was used for testing, following a standard set of procedures recommended by the NCCLS. In this methodology, a set of discs saturated with either testing compounds or a control was placed on inoculated agar plates. The plates were inoculated with organisms listed in the tables provided in FIG. 6, including *C difficile, P. acnes, C. prefringens, L. casei, C. albicans, E. coli*, ATTC 8739 and ATCC 43895, *S. aureus, S. mutans, S. pyogenes, P. aeruginosa* and *K. pneumonia*. The control sample was amoxicillin, an antimicrobial with very effective broad spectrum antibiotic properties. Samples included delphinidin, pelargonidin, cyanidin CI, 28% cyanindin-3-glucoside (C3G), protocatechuic acid (PCA) and 2,4,6 Trihydroxybenzaldehyde (2,4,6 THBA).

After 18, 24, or 48 hours of incubation, depending upon the microorganism, each plate was examined. The diameters of the zones of complete inhibition were measured, including the diameter of the disc. Zones were measured to the nearest millimeter, using sliding calipers. The size of the zones of inhibition was interpreted by referring to NCCLS standard. Results were interpreted as follows: NI was no inhibition of growth under the test sample, I was inhibition of growth under the test sample, NZ indicated no zone of inhibition surrounding the test sample, and CZ indicated a clear zone of inhibition surrounding the sample and zone width in millimeters. See FIG. 6 for complete results.

Results

Referring to FIG. 6 and FIG. 32, the testing samples had bactericidal and bacteriostatic activity against many of the organisms. Of note, *P. acnes*, an organism that is very difficult to treat, often requiring multiple current antibiotics for effective treatment, was susceptible to both C3G and PCA. Indeed, both of these test samples were bactericidal against *P. acnes*. Additionally, PCA was also effective against *Staphylococcus aureus* ATCC 33591, known as Methacillin Resistant Staph *Aureus* (MRSA), *Staphylococcus epidermidis* ATCC 51625, known as Methacillin Resistant Staph *Epidermidis* (MRSE), *E. coli* 8739 and 43895, and *Legionella* 43662.

PCA was also shown to have some effectiveness against *Pseudomonas aeruginosa*, a common pathogen in wounds, especially burns, as well as chronic lung infections. Amoxicillin, the control sample, had no effect on *P. aeruginosa*. Similarly, *Candida albicans*, frequently a co pathogen in wounds, was susceptible to PCA.

PCA was also shown to have some effectiveness against *Pseudomonas aeruginosa*, a common pathogen in wounds, especially burns. Amoxicillin, the control sample, had no effect on *P. aeruginosa*. Similarly, *Candida albicans*, frequently a co pathogen in wounds, was susceptible to PCA.

In summary, the present invention provides advantages over the prior art, including providing anthocyanin, anthocyanidin, their metabolites or combinations thereof to a wound to provide a reduction or elimination of bacteria. It is contemplated that the invention will also find use in the treatment of surfaces, including medical devices and medical implants, to reduce or eliminate bacteria.

Example 2: Use of Mouse Model to Determine Dose Levels and Intervals of Test Samples Methods:
Mice had back skin tape stripped and the stripped site (wound) was infected with *P. aeruginosa* (ACTA 9027). The test reagents were applied topically in an aqueous solution on the stripped site at two hours and daily for four days.

Cyanidin 3-glucoside (C3G), an anthocyanin, and its main metabolite PCA were formulated and tested at several doses. The aqueous carrier was water. The C3G formulation included 50 mM, 100 mM and 200 mM dose concentrations. Similarly, the PCA formulation included at 50, 100 and 200 mM dose concentrations.

Results
Results were collected from the mice at day five. Both C3G and PCA decreased the bacterial burden; however, none were statistically significant. See FIG. 9A. There was a trend towards a decreasing concentration of PCA, with 50 mM being the most effective. The most effective dose of C3G was 100 mM. It is contemplated that because C3G degrades to PCA in this environment, the test results may indicate that C3G was not being tested alone, but rather was a combination of C3G and its metabolites, including a combination of C3G and PCA as the effective agents.

Example 3: Use of Mouse Model to Further Determine Effective Dose Levels and Dose Intervals of Test Samples Methods:
Mice had back skin tape stripped and the stripped site (wound) was infected with *P. aeruginosa* (ACTA 27853). The test reagents were applied topically in an aqueous solution on the stripped site at two hours and daily on day 1, 2 and 3.

C3G, an anthocyanin and its main metabolite PCA were formulated and tested at several doses. The aqueous carrier was water. The C3G formulation included 100 mM and 200 mM dose concentrations and the PCA formulation included 25 and 50 mM dose concentrations.

Results
Results were collected from the mice at day two and four. Both C3G and PCA decreased the bacterial burden at 48 and 96 hours. (See FIG. 9B). The most significant decrease of bacteria was observed at 25 mM of and 100 and 200 mM of C3G. Although PCA at 25 mM reduced the bacterial burden at both time periods, its activity was statistically significant at 48 hours. C3G at both 100 mM and 200 mM significantly reduced the bacterial burden at 48 and 96 hours.

Example 4: Use of a Mouse Model for Wound Healing

Methods:
Mice were shaved but unstrapped and uninfected (normal rodent skin). The test reagents were applied topically in an aqueous solution on the unstripped site at two hours and daily on day 1, 2 and 3.

Testing reagents consisted of C3G and PCA formulated at one dose, 100 µM in an aqueous solution.

Figure 10A:
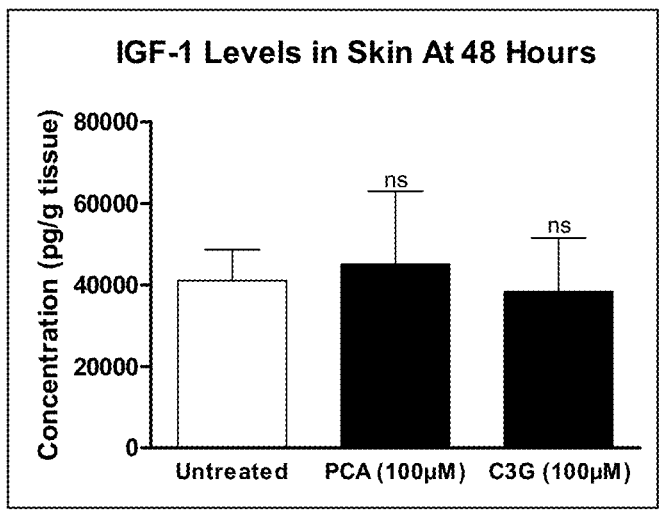
FIG. 10A shows the results of an additional rodent back skin tape study to determine effective dosages of PCA and C3G in a vehicle of water that would be bactericidal for *P. aeruginosa.
Figure 10B:
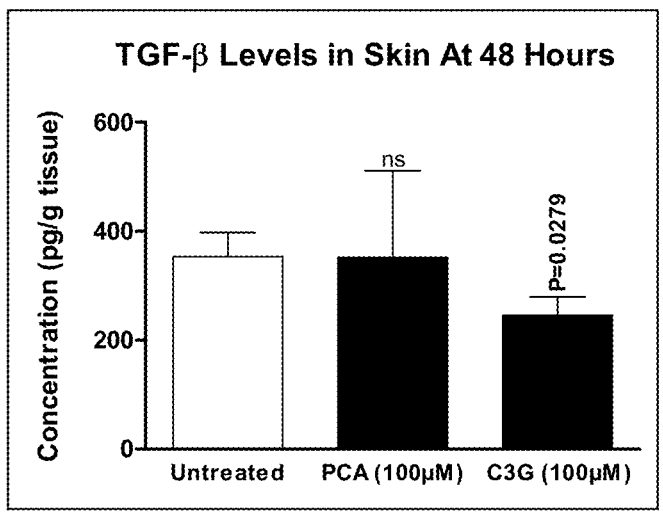
* FIG. 10B shows the results of an additional rodent back skin tape study to determine effective dosages of PCA and C3G in a vehicle of water that would be bactericidal for *P. aeruginosa.
Figure 10C:
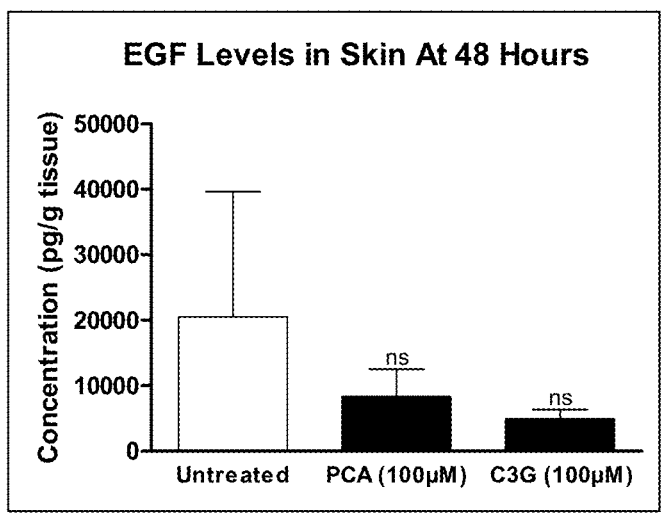
* FIG. 10C shows the results of an additional rodent back skin tape study to determine effective dosages of PCA and C3G in a vehicle of water that would be bactericidal for *P. aeruginosa.*

Results:
Referring to FIG. 10, there was little or no stimulation of IGF-1 and TGF-$\beta$ at local levels observed at the 100 µM concentration of testing reagents. In fact, levels of EGF actually decreased below normal levels. There was observed a decrease of all three local growth hormones at 100 uM of C3G. These results suggest that mice skin differs in response to a dose that has been shown to stimulate human synovium to produce IGF-1. Thus, this low of a dose is not useful for rodents for this purpose.

Example 5: Use of Mouse Model to Determine Isolated Effect of 25 mM Solution of PCA in Various Environments Methods:
Four different conditions were used: mice had back skin tape stripped and the stripped site (wound) was infected with *P. aeruginosa*; mice had back skin stripped and were not infected, mice had taped stripped, infected and treated with PCA, mice were tape stripped, uninfected, and treated with PCA. When used, the PCA test reagent was applied topically in an aqueous solution on the stripped site at two hours and 24 hours.

The testing reagents consisted of and PCA formulated at one dose, 25 mM, in an aqueous solution. Levels of IGF-1, TGF-$\beta$, and EGF levels in the skin tissue at 48 hours were measured by ELISA. There were two control groups; the stripped skin and the stripped skin and infected.

Results:
Referring to FIG. 13, the infected stripped skin showed the highest level with IGF-1 (statistically significant) and TGF-$\beta$. This is representative of tissue response to injury and infection; similarly, the EGF response was very inconsistent compared to the other two growth hormones.

The EGF response levels were different than either IGF-1 or TGF-$\beta$. They were highest in the stripped and uninfected wound and lowest in the stripped, infected and treated wound. Therefore, the treatment optimized the amount of hormone production compared to the untreated infection. This is beneficial to limit scarring while promoting healing over the controls. Overall, PCA at 25 mM acts on stripped and infected mice skin and optimizes the IGF-1 production and optimizes the local growth hormones.

Example 6: Use of Mice to Establish Wound Promoting Effect of Compositions

Method:
Fifteen rodents were used to establish the histological findings of stripped skin, stripped and infected skin, and stripped, infected and treated wound. There were two control groups and four experimental groups according to the following:

Control Group 1: three mice with only tape stripped wounds on the back. These mice were not infected or treated. The skin was harvested at time zero, 2 and 48 hours for histology examination.

Control Group 2: three had tape stripped wounds and infection. Tissue submitted at 2 and 48 hours for histological examination.

Experimental Groups: There were 4 experimental groups. In these groups, mice had skin stripped wounds and infection. Treatment varied by reagent and dosage. Testing reagents included PCA at 25 at 25 and 50 mM and C3G at 100 and 200 mM.

*Pseudomonas aeruginosa* (ATCC 27853) Procured from American Type Culture

Collection, Manassas, Va. was used to infect the experimental groups of mice. The organism was grown overnight at 37° C. at ambient atmosphere trypticase soy agar plates supplemented with 5% sheep blood cells. The culture will be aseptically swabbed and transferred to tubes of trypticase soy broth. The optical density will be determined at 600 nm. The cultures will be diluted to provide an inoculum of approximately 9.0 $\log_{10}$ CFU per mouse in a volume of 100 µL. Inoculum count was estimated before inoculation by optical density and confirmed after inoculation by dilution and back count.

The testing reagents were topically applied at 2 and 24 hours with 100 uL of fluid spread over the wound.

The following histological assessments were conducted:

Surface Cellularity: The histological assessment included the presence or absence of the surface cellularity and the depth of the cells.

Dermis: vascularity and inflammation.

Thickness: The thickness of the dermal layer was observed.

Hair Follicles: The hair follicles and the layer of surrounding cells were observed. Hair follicles presence is critically important to skin wound healing. (Gharzi A, Reynolds A J, Jahoda C A. Plasticity of hair follicle dermal cells in wound healing and induction. Exp Dermatol. 2003 April; 12 (2):126-36). The dermal sheath surrounding the hair follicle has the progenitor cells for contributing fibroblasts for wound healing. (Johada C A, Reynolds A J. Hair follicle dermal sheath cells: unsung participants in wound healing. Lancet. 2001 Oct. 27; 358(9291):1445-8).

Vascularity: Vascularity was observed, but an assessment of angiogenesis was not performed on the 48 hour material since new vascularity takes three to twelve days to develop. (Busuioc C J, et al. Phases of cutaneous angiogenesis process in experimental third-degree skin burns: histological and immunohistochemical study. Rom J Morphol Embryol. 2013; 54(1):163-710.)

Inflammation: The presence of cellular infiltration was observed and its location.

Skin Thickness: The thickness of the skin was estimated related to the uninfected, untreated wound. This depth was estimated on the uniform histology photomicrographs from the surface to the muscle layer.

Results:

The following results were observed in each group:

CONTROL GROUP 1: Uninfected and untreated.

Figure 14:
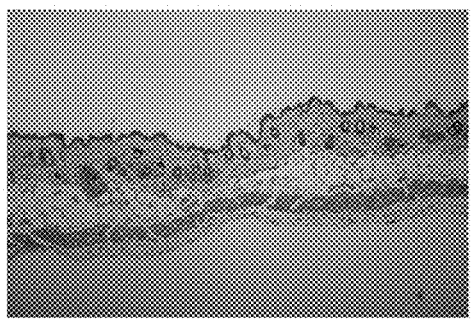
FIG. 14 is a photographic image of a cross section of rodent skin.
Figure 15:
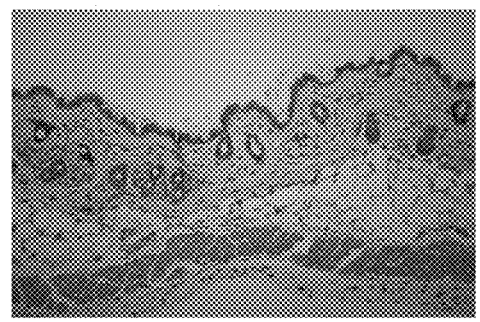
FIG. 15 is a photographic image of a cross section of rodent skin.

Time Zero: (See FIGS. 14-15) At time zero following the wound stripping there was cellular covering of the surface. The dermal layer was not thickened. The hair follicles have a single cellular lining. There was minimal vascularity and no inflammation. The depth of the tissue was considered zero for future bench mark. 0+

Figure 16:
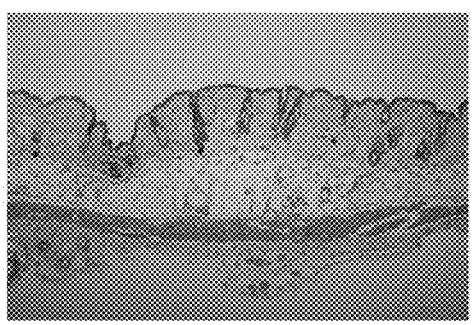
FIG. 16 is a photographic image of a cross section of rodent skin.
Figure 17:
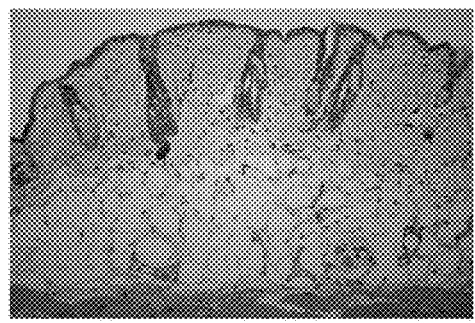
FIG. 17 is a photographic image of a cross section of rodent skin.

2 hours: (See FIGS. 16-17) At 2 hours following the wound stripping the surface remained covered with cellularity. The dermal layer was minimally thickened. The follicles and cellular lining was the same. There was minimal increase in vascularity and inflammation. The increase in the depth of the tissue was considered 0.5+.

Figure 18:
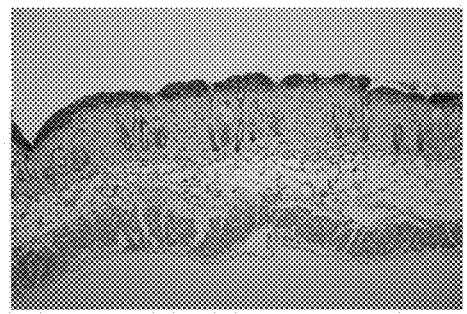
FIG. 18 is a photographic image of a cross section of rodent skin.
Figure 19:
FIG. 19 is a photographic image of a cross section of rodent skin.

48 hours: (See FIGS. 18-19) At 48 hours the wound stripped, uninfected, untreated specimens showed natural history response of surface cellular proliferation and thickness. The dermal layer was thickened. The hair follicles were present with single layer cellular lining. The vascularity was increased in amount compared to the 2 hour specimens. The inflammation was present throughout the dermis and muscle layer. The thickness was considered 0.5+.

Control Group 2: Infected and Untreated.

Figure 20:
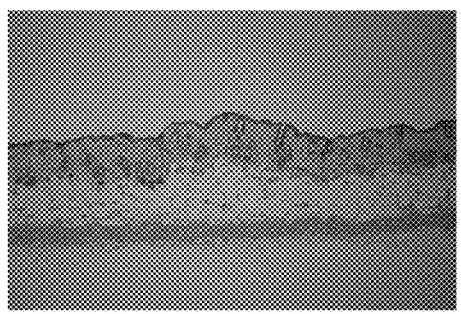
FIG. 20 is a photographic image of a cross section of rodent skin.
Figure 21:
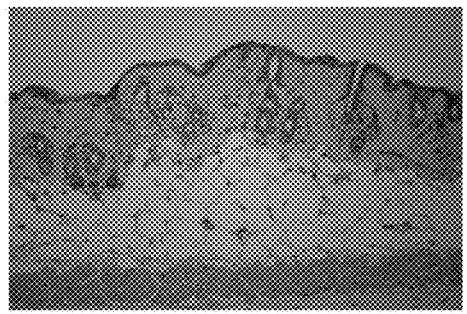
FIG. 21 is a photographic image of a cross section of rodent skin.

2 hours: (See FIGS. 20-21) The histological assessment showed the wound stripped, infected, but untreated controls at 2 hours to have multiple cellular covering on surface. There was minimal thickening of the dermal layer. The hair follicles were abundant and had double layer cellular lining. There was minimal vascularity and no inflammation in the specimens. The thickness was assigned 0.5+.

Figure 22:
FIG. 22 is a photographic image of a cross section of rodent skin.
Figure 23:
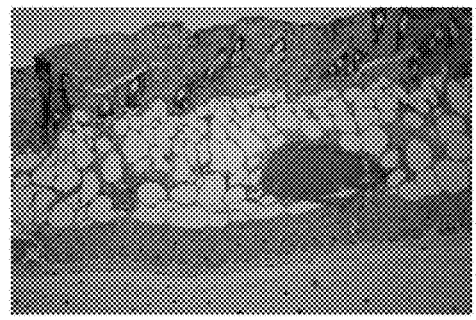
FIG. 23 is a photographic image of a cross section of rodent skin.

48 hours: (See FIGS. 22-23) At 48 hours the surface cellular covering was gone. The dermal layer had minimal thickening. The hair follicles were present, with minimal cellularity lining. There was marked increase in vascularity and minimal inflammation in dermis layer. The depth was considered 0.5+ compared to time zero.

Figure 24:
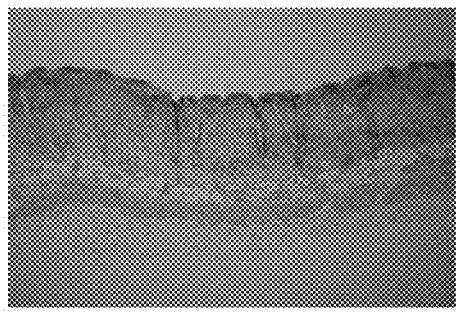
FIG. 24 is a photographic image of a cross section of rodent skin.
Figure 25:
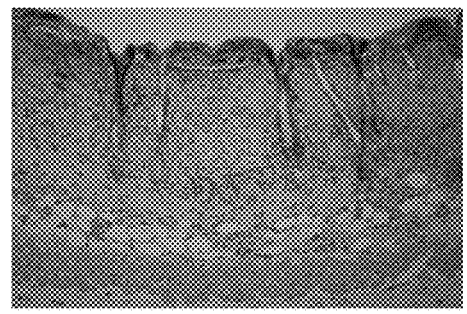
FIG. 25 is a photographic image of a cross section of rodent skin.

Experimental Group PCA 25 mM 48 hours: (See FIGS. 24-25) The cellular covering of the surface was abundant and multiple cell layers. The dermal layer was thickened. The hair follicles were prominent with multiple cellular lining. There was collagen proliferation between the epidermis and dermis. Additionally, there was moderate vascularity, but less than that seen in infected untreated group. There was abundant inflammation and it was greater than was seen in the PCA 50 dose. Thickness was assigned 2+.

Figure 26:
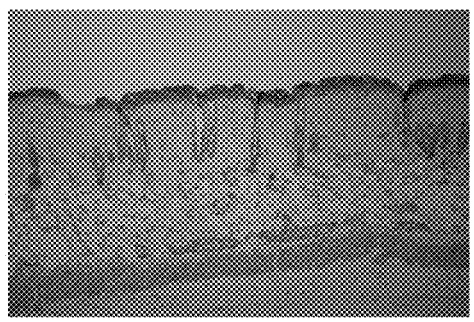
FIG. 26 is a photographic image of a cross section of rodent skin.
Figure 27:
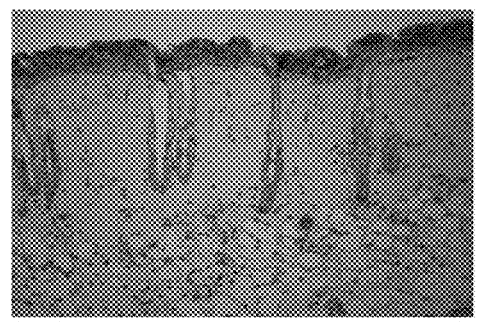
FIG. 27 is a photographic image of a cross section of rodent skin.

Experimental Group PCA 50 mM 48 hours: (See FIGS. 26-27) The surface was covered with multiple layers of cells. The dermal layer was thicker. The hair follicles had double layer of cells. There was increased vascularity. Inflammation also increased in the dermis and below the muscle layer. The tissue thickness was assigned 2+.

Experimental Group C3G 100 mM

Figure 28:
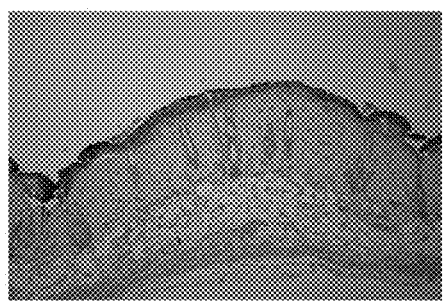
FIG. 28 is a photographic image of a cross section of rodent skin.
Figure 29:
FIG. 29 is a photographic image of a cross section of rodent skin.

48 Hours: (See FIGS. 28-29) There was multiple cellular covering of the surface. The dye of the C3G was apparent on the skin surface indicating it had not changed color due to pH nor completely degraded. The dermal layer was thicker. The hair follicle had single and double cellular lining. The vascularity was prominent. There was inflammation in the dermis and muscular layer and below. The thickness of the tissue was assigned 2+.

Experimental Group C3G 200 mM

Figure 30:
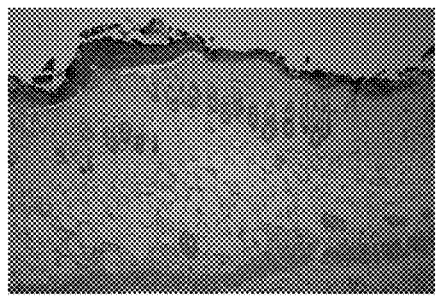
FIG. 30 is a photographic image of a cross section of rodent skin.
Figure 31:
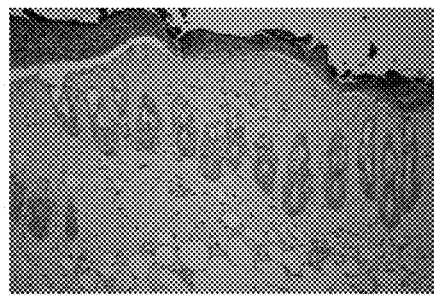
FIG. 31 is a photographic image of a cross section of rodent skin.

48 Hours: (See FIGS. 30-31) There was evidence of the C3G material remaining on the skin surface. The surface cellular layer was multiple cells thick. The dermal layer was thickened. The hair follicles had single and double cellular lining. The vascularity was increased. There was inflammation in the dermis and muscular layer. The thickness was assigned 2+.

These results confirm that an anthocyanin (~38% C-3-G as the source) and the main metabolite of anthocyanins and anthocyanidins, protocatechuic acid (PCA) when applied topically at various calculated doses to the stripped skin wound of a rodent were bactericidal in 48 to 96 hours. There was a 10,000 fold kill of *Pseudomonas aeruginosa* in 48 hours with both reagents and dose.

The results also show by histology a simultaneous healing of the experimentally created wound in the same time frame. C-3-G and PCA in two different doses stimulated tissue repair as evidence by histology.

Specifically, the experimental model provided evidence of a histological contrast between the control and experimental groups. At 48 hours, Control Group 2 that was wound stripped and infected showed a clear contrast to the uninfected Control Group 1. In the skin stripped infected group there was loss of the epithelial cellular covering, no follicular cellular proliferation, marked increase in vascularity and little inflammatory response. This histological condition provided clear contrast to the treatment groups. All treatment groups by comparison showed healing response with multiple layer cellular proliferation on the surface, multiple layer cellular proliferation along the hair follicles, less vascularity, but an inflammatory cellular response in the dermis and muscular levels. See FIGS. 14-31. PCA at a concentration of 25 mM also showed collagen layer formation between the epidermis and dermis. (See figures/photos 24 and 25). This response is beneficial in the use of anthocyanin and anthocyanidins and metabolites thereof as a cosmetic agent to promote wound healing and improve skin health, including wrinkle reduction or removal. This method of use of anthocyanin and anthocyanidin metabolites, and particularly PCA, is based upon the two fold response; the collagen layer increase and the skin swelling that increased the depth of the skin.

Example 7: PCA's Effect on *Pseudomonas Aeruginosa* ATCC 700888 and *Staphylococcus aureus* ATCC 33591 (MRSA) Biofilms The inventor has shown that a composition comprising PCA was able to stop the growth of a biofilm formation as well as destroy already formed biofilms. The biofilms tested were *Pseudomonas Aeruginosa* ATCC 700888 and *Staphylococcus aureus* ATCC 33591 (MRSA).

The following amounts were tested on a polyester cloth and sintered 316 stainless steel mesh: The cloth was a piece cut from a polyester pillow case. The cloth was soaked in the PCA solution and air dried for 24 hours. The cloth was dried when tested.

1: 20 grams of PCA in 100 ml of 70% isopropyl alcohol, vehicle: cloth material, 1-1
2: 20 grams of PCA in 100 ml of 70% isopropyl alcohol, vehicle: cloth material, 1-2
3: 20 grams of PCA in 100 ml of 70% isopropyl alcohol, vehicle: 3-ply sintered mesh, 1-1
4: 20 grams of PCA in 100 ml of 70% isopropyl alcohol, vehicle: 3-ply sintered mesh, 1-2
5: 20 grams of PCA in 100 ml of 70% isopropyl alcohol, vehicle: 5-ply sintered mesh, 1-1
6: 20 grams of PCA in 100 ml of 70% isopropyl alcohol, vehicle: 5-ply sintered mesh, 1-2
7: Glass Slide (to serve as control article), 1-1
8: Glass Slide (to serve as control article), 1-2
9: PCA crystals imbedded, vehicle: 3-ply sintered 40 micron mesh, 1-1
10: PCA crystals imbedded, vehicle: 3-ply sintered 40 micron mesh, 1-2
11: PCA crystals imbedded, vehicle: 5-ply sintered 40 micron mesh, 1-1
12: PCA crystals imbedded, vehicle: 5-ply sintered 40 micron mesh, 1-2

The bacteria (*Pseudomonas Aeruginosa* ATCC 700888 and *Staphylococcus aureus* ATCC 33591 (MRSA)) were placed in reactors and allowed to grow and form biofilms. Then cloths and metal were treated by coating with PCA solutions and then were left to dry. Two sets of the stainless steel mesh had crystals imbedded into the mesh to replicate placement into a mesh or coated joint implant. A standard ASTM E-2647 drip flow biofilm reactor was used to grow a biofilm and the treated surfaces (as well as the control) were placed into the reactors and the biofilm was allowed to grow for about 6 hours. The samples received a continuous nutrient flow for an additional time period for about 48 hours to promote a steady growth rate of the biofilm. Then the biofilm was removed, analyzed and a microbial count and log density measurements were taken for each sample. Colony forming unites ("CFU") were counted (which is an estimate of the number of viable bacterial. Log density is the calculation of the biofilm present.

It was found that A 10% concentration as not as effective against *Pseudomonas*, but a 20% concentration of PCA was very effective. See FIGS. 33 and 34. FIG. 34 shows that the materials that were treated had a very much smaller log density and CFUs than the control material (glass slide).

It was found that a 30% concentration of PCA against MRSA was very effective. See FIGS. 35 and 36.

Example 8: Spray on Solution of PCA and Time Study of PCA's Effect on *Pseudomonas Aeruginosa* ATCC 700888 and *Staphylococcus aureus* ATCC 33591 (MRSA) Biofilms Next the time necessary to destroy biofilms and kill bacteria was tested. A biofilm consisting of over 10 million organisms were formed on a glass slide. A single spray of 30% PCA mixed with isopropyl alcohol was applied to the glass slide. The colony forming units (CFU) were examined at 30 minutes and 60 minutes after the single spray. Incidentally, typical tests for testing the ability of an antibiotic to work are done for 48 hours. The tests performed were as follows:

Glass slides were inoculated at Time 0. Batch phase was performed for 6 hours to allow for biofilm formation on the glass slides. The drip flow mechanism was then turned on to provide a continuous flow of nutrients to the glass slides over 48 Hours. After 48 hours, 2 sets of glass slides were sprayed with a 30% PCA solution. One set was removed and analyzed for biofilm reduction after 30 minutes. The other set was removed after 60 minutes.

2 sets of control slides were also removed and analyzed after 30 minutes and 60 minutes. The control slides were not treated with 30% PCA and were used for comparative purposes.

The Log Reduction Calculations were performed as follows: The mean 30% PCA treated samples were compared to the mean positive control samples, per time point evaluated.

For *Pseudomonas aeruginosa*, after 30 minutes of the application of the 30% PCA spray, there was a 3.3 log reduction. After 60 minutes, there was 2.2 log reduction, which amounts to a 99.9% reduction in the number colony forming units. See FIG. 37.

For *Staphylococcus aureus*, after 30 minutes of the application of the 30% PCA spray, there was a reduction of 60 million CFUs to 3 million and after 60 minutes, there was reduction, of 25 million to 2 million CFUs. See FIG. 38.

Thus, the results show that a 30% PCA spray killed 90% of the biofilms in 30 minutes. The FDA only requires a 90% reduction.

It is noted that this above experiment was chosen to replicate a clinical condition, involving a metal or linen implant even to the extreme because there would never be that high of a concentration of biofilms nor bacteria in practice flowing over the implants. Accordingly, the invention also provides a method of blocking initial attachment of the bacteria to the implant and therefore preventing growth/development of a biofilm on an implant.

Example 9: Testing Against *Propionibacterium acnes*

BALB/c mice were infected with *Propionibacterium acnes* via intradermal injection and treated topically with varying concentrations of a novel test compound, PCA, at 2, 24, 48 and 72 hours following challenge. Efficacy was evaluated by CFU analysis from skin samples harvested at 96 hours post challenge.

These data demonstrate that *P. acnes* establishes a steady intradermal colonization in the skin of BALB/c mice. When administered topically, PCA at 60 mg/kg, demonstrated a bacteriostatic effect and reduced *P. acnes* CFU burden in mouse skin by a statistically significant amount. All lower amounts of PCA showed no such effect.

Female BALB/c mice, ordered from Harlan and weighing 17-19 g, were acclimated to housing conditions and handled in accordance with AUP number TP-18-13. The animals were acclimated for 4 days prior to bacterial challenge. Only animals deemed healthy and fully immunocompetent were included in this study. Cages were prepared with 2 mice per cage.

The animals were fed Teklad Global Rodent Diet (Harlan) and water ad libitum. Mice were housed in static cages with Teklad ⅛" corn cob bedding inside bioBubble® Clean Rooms that provide H.E.P.A filtered air into the bubble environment at 100 complete air changes per hour. All treatments and infectious challenges were carried out in the bioBubble® environment. The environment was controlled to a temperature range of 74°±4° F. and a humidity range of 30-70%. Treatment groups were identified by cage card. All procedures carried out in this experiment were conducted in compliance with all the laws, regulations and guidelines of the National Institutes of Health and with the approval of the TransPharm Animal Care and Use Committee.

Bacterial Cultures

*Propionibacterium acnes* (1100; ATCC 6919), procured directly from the American Type Culture Collection.

Skin Preparation

On Day −1, each mouse was anesthetized in an Isoflurane induction chamber and the lesion site was cleared of hair. An area of approximately 2.0 cm×2.0 cm of skin on the dorsal area of each mouse was cleared through use of the depilatory agent Nair®.

Challenge

Cultures were grown for 96 hrs at 37° C. in an anaerobic atmosphere on TS agar plates supplemented with 5% sheep blood cells. The culture was aseptically swabbed and transferred to tubes of TS broth and allowed to grow for 72 hours. The cultures were diluted to provide challenge inoculum of approximately 6.0-7.0 log 10 CFU per 50 μL in PBS. On Day 0 each mouse was anesthetized using Isoflurane. Each animal on the study was administered 50 μL of the bacterial suspension via intradermal injection in the dorsal area that was previously denuded of hair. The final CFU count from the challenge suspension determined that 6.0 log 10 CFU per mouse were delivered.

Formulation and Dosing

The test treatment, PCA, was provided by the study Sponsor and formulated using sterile water. Treatments were administered topically in a dose volume of 0.1 mL. Treatments were given at 2, 24, 48 and 72 hours post challenge at 60 mg/kg (78 mM; Group 3), 30 mg/kg (39 mM; Group 4) or 15 mg/kg (19.5 mM; Group 5).

TABLE 1

Animal Challenge, Treatment and Harvest Schedule

| Group | n | Intradermal P. acnes | Treatment | ROA | Schedule | CFU harvest* |
|---|---|---|---|---|---|---|
| 1 | 2 | 6.0 log | untreated | NA | NA | 2 hr |
| 2 | 2 | 6.0 log | untreated | NA | NA | 96 hr |
| 3 | 2 | 6.0 log | PCA 60 mg/kg | Topical | 2, 24, 48, 72 hrs | 96 hr |
| 4 | 2 | 6.0 log | PCA 30 mg/kg | Topical | 2, 24, 48, 72 hrs | 96 hr |
| 5 | 2 | 6.0 log | PCA 15 mg/kg | Topical | 2, 24, 48, 72 hrs | 96 hr |

*Relative to Challenge at 0 hr

Results and Discussion

Infection/Treatment/General Observations

None of the study subjects displayed any acute adverse events associated with the treatments. None of the test subjects succumbed to the infection or showed signs of morbidity, which could be attributed to penetration of the infection into the circulatory system or deep tissue. No treatment group displayed adverse signs beyond those expected for mice which have received a superficial bacterial infection.

The test article preparations were administered topically at 2, 24, 48 and 72 hours following the bacterial challenge. While untreated mice were harvested at 2 hours post infection, CFU burden was not detected. However at 96 hours post infection, the CFU burden rose from 6.0 log 10 to 6.65 log 10, indicating a successful inoculation.

At 96 hours following challenge, mice were humanely euthanized and skin was aseptically removed from the infection site. Skin samples were placed in homogenation vials with 2.0 mL PBS, weighed and homogenized using a mini-bead beater. Homogenate was serially diluted and plated anaerobically on TSA agar plates for enumeration of colony forming units per gram of skin tissue.

Figure 39:
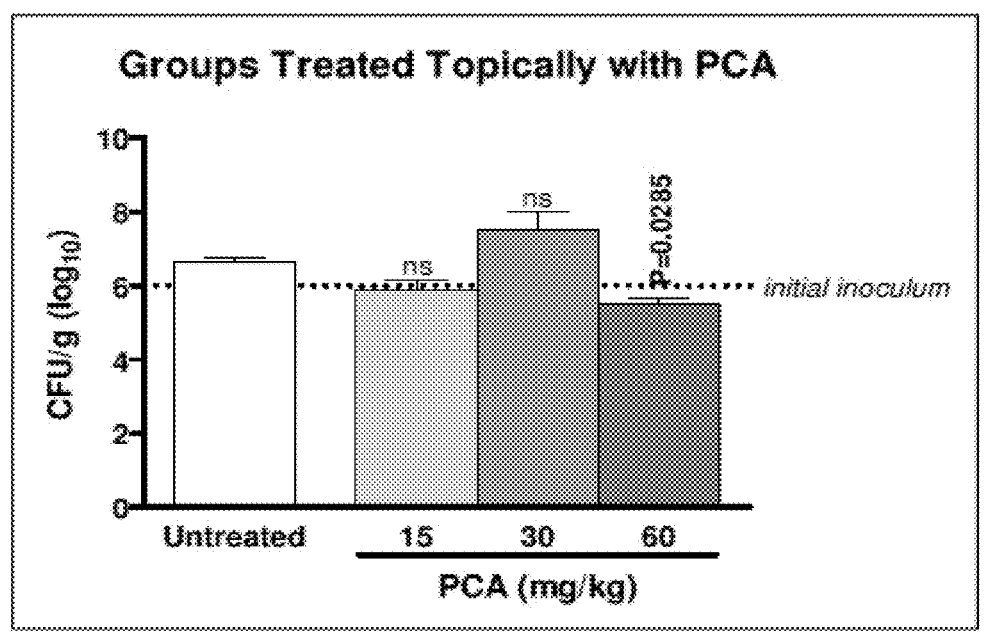
FIG. 39 provides a chart of results of testing PCA against *P. acnes* on the skin.

The mean bacterial burden of the untreated group at 96 hours was 6.65 log 10. CFU levels in all treated groups were compared to the untreated group to determine statistical significance. Only the high dose of PCA (60 mg/kg) showed significant reduction of CFU burden when compared to the untreated control (P=0.0285). That an approximately 1 log 10 reduction was observed indicates that at this concentration PCA, is bacteriostatic and not bactericidal. All other treatments were statistically non-different than the untreated control (FIG. 39).

These data demonstrate that *P. acnes* establishes a steady intradermal colonization in the skin of BALB/c mice. When administered topically, PCA at 60 mg/kg (78 mM solution), demonstrated a bacteriostatic effect and reduced *P. acnes* CFU burden in mouse skin by a statistically significant amount. All lower amounts of PCA showed no such effect.

Example 10: Antibiotic Testing with PCA or 246 THBA Using Propylene Glycol

PCA or 246 THBA were combined with propylene glycol (PPG). The PPG was placed on a paper disc and then either PCA or 246 THBA was applied. The paper disc was then placed on colonies of various bacterial in a Petri dish. At a certain uniform time they were inspected and classified in the following categories:
  NI: no inhibition of bacteria growth under the sample
  I: inhibition of bacterial growth under the sample
  NZ: no accompanying zone of inhibition
  CZ: clear zone of inhibition surrounding the sample and zone measured in millimeters (mm).

The results were as follows:
Water/PCA/*Klebsilla pneumonia* ATCC4352: I/CZ/2 mm
PPG/PCA/*Klebsilla pneumonia* ATCC4352: I/CZ/3 mm
Water/PCA/*Pseudomonas aeruginosa* ATCC9027: I/CZ/10 mm
PPG/PCA/*Pseudomonas aeruginosa* ATCC9027: I/CZ/4 mm
Water/246 THBA/*Pseudomonas aeruginosa* ATCC9027: I/CZ/2 and 3 mm
PPG/246 THBA/*Pseudomonas aeruginosa* ATCC9027: I/CZ/3 mm
Water/246 THBA/*Staphylococcus aureus* ATCC33591 (MRSA): I/CZ/14 and 15 mm
PPG/246 THBA/*Staphylococcus aureus* ATCC33591 (MRSA): I/CZ/12 mm Example 11: PCA to Sterilize/Disinfect Human Skin Study A randomized double blinded study was performed at Loma Linda Medical School. It involved 4 phases over two years' time. The methods were as follows:

Phase 1: The active test reagent was topically applied 1.54% PCA in sterile water to the anterior shoulder region. This 1.54% solution of PCA in water was used effectively in our prior animal wound studies. The controls were Chloroprep (2% Chlorhexidine in 70% isopropyl alcohol) and Betadine (9.0% to 12.0% available iodine in water). Cultures were taken before application and 20 minutes after application. The initial harvest was by a surface swab. Application was by soaked sponge, without force or scrubbing. The second harvest was performed with the back edge of a sterile knife blade scraping with pressure in attempt to maximize the harvest from the deeper sebaceous glands and hair follicles. The specimens were placed in culture media. Bacteriology was performed at WuXiAppTec in Marrietta, Ga.

Phase 2 included eleven medical students and was same method as Phase 1. However the PCA vehicle was changed to 70% isopropyl alcohol. This allowed a higher concentration of PCA than possible in sterile water, 10%. Phase 2a: The 70% isopropyl alcohol vehicle was tested for its bactericidal properties. All cultures that were negative or markedly reduced with PCA topical solution were examined for exact nature of the index bacteria and the post treatment cultures that showed no or minimal growth. In this way it was learned what specific bacterial strains PCA could eliminate or reduce.

Results:
Phase 1 showed the aqueous solution of 1.54% PCA to be partially effective as compared to the controls. In phase 1 of the Loma Linda Studies, 1% PCA in water showed no growth in 7 of 22 subjects on aerobic culture and 10 cultures showed reduced growth. By anaerobic culture, 6 of 22 cultures showed no growth and 15 showed reduced colony growth. Six heavy growth pre-treatment cultures prior to the 1.24% PCA treatment were chosen to examine the isolates to learn what pathogens were killed or not killed. Most of the bacteria eradicated were non pathogens. Sample culture #29 showed 5 unique colonies by aerobic culture and 2 unique colonies by anaerobic culture. After 1.24% PCA treatment there was no growth on either culture. Therefore pretreatment cultures were examined for the species. The chart below is the result of the specific species colony identified and the method of identification used. The organisms were predominately non pathogens except for *P. acnes*. However all of which were removed by the treatment.

| SAMPLE ID | GRAM STAIN & CELL MORPHOLOGY | ORGANISM IDENTIFICATION | METHOD OF IDENTIFICATION |
|---|---|---|---|
| 1(A) | Gram positive cocci | *Micrococcus luteus/lylae* | Biochemical Analysis |
| 1(B) | Gram positive cocci | *Micrococcus luteus/lylae* | Biochemical Analysis |
| 1(C) | Gram positive cocci | *Micrococcus luteus* | Biochemical Analysis |
| 1(D) | Gram positive cocci | *Micrococcus luteus* | Biochemical Analysis |
| 1(E) | Gram positive cocci | *Staphylococcus epidermidis* | DNA Sequencing |
| 2(A) | Gram positive cocci | *Staphylococcus capitis* | Biochemical Analysis |
| 2(B) | Gram positive rods | *Propionibacterium acnes* | DNA Sequencing |

Two other index pre-treatment cultures showed heavy growth of *Propionibacterium acnes*, a potential pathogen. The post treatment cultures showed the colonies of *P. acnes* was decreased to 5 colonies in one and 1 colony in another, but not eliminated. This suggested that PCA may be effective against *P. acnes* if a higher concentration was applied in subsequent Phases of this study. Testing with 1.24% in water killed bacteria of normal flora as shown above chart. To increase efficacy and to improve skin penetration to the depth of the hair follicles that can harbor bacteria, Phase II of the study used 70% isopropyl alcohol (30% water) 85 ml so as to increase the concentration of PCA.

Phase II: This study involved 11 human subjects. There were 5 Males and 6 females. The ages were 23-33 years. There were two reagents. The control was 70% isopropyl alcohol. The PCA source was a phytochemical extract from Nanjing Zelang Medical Technology Co. LTD. This source was chosen due to markedly reduced cost of goods compared to that which is biochemically manufactured. The experimental dose was 9+/−% PCA in 70% isopropyl alcohol. 10 grams of PCA was placed in 100 ml of isopropyl alcohol. The isopropyl alcohol allowed for a greater dose of PCA than water. (allowed more PCA to be dissolved). The initial harvest was by a surface swab. Application was by soaked sponge, without force or scrubbing. The second harvest was performed with the back edge of a sterile knife blade scraping with pressure in attempt to maximize the harvest from the deeper sebaceous glands and hair follicles.

Cultures were stored in ice and shipped in FedEx ice box to WuXiapptec in Marietta, Ga. for aerobic and anaerobic cultures and held for 21 days. Method used for bacterial species identification was Vitek® MS-MALDI-TOF MS. It was determined that the dose or concentration of PCA needed to be increased, which required changing the water to 70% isopropyl alcohol. This is the same as used with Chloroprep® which is 2% w/v chlorhexidine gluconate in 70% isopropyl alcohol. 10% PCA in 70% isopropyl alcohol was compared to the control 70% isopropyl alcohol in Phase II. The results of Phase II showed the following summary of the no growth culture results after treatment.

|  | Aerobic | Anaerobic |
|---|---|---|
| PCA/IP alcohol | 10/11 no growth | 9/11 no growth |
| Control IP alcohol | 6/11 no growth* | 4/11 no growth |

*Note that 3/11 of the 70% IPA groups showed increased colony growth after IPA treatment alone.

Phase 2 results with 9+% solution of PCA were compared to similar test Phase 1 and this showed this to comparable to Betadine in effectiveness, but not with Chloroprep, which killed all the bacterial colonies. This PCA/70% isopropyl alcohol solution was effective against 10/11 index cultured aerobic bacteria and reducing on anaerobic culture in 9 of 11 subjects. The two showing residual colonies were one (n=1) colony of *Propionibacterium acnes* in each of the two cultures. Phase 2a showed that 70% isopropyl alcohol (IPA) alone had few antibacterial properties. Of course sterile water used in Phase 1 had no antibacterial properties, therefore the testing was on the effectiveness of the PCA.

The Phase 2 study showed the importance of PCA reagent concentration or dose. A different application necessitated an increase dose. PCA at 1.54% although effective in an animal open skin wound was not a very effective antibacterial reagent on intact human skin. Therefore the concentration of PCA needed to be increased and could not be increased with water, but only be accomplished with the vehicle of 70% isopropyl alcohol.

Phase 2 showed that PCA was more effective in the higher concentration eliminating all bacteria and reducing *Propionibacterium acnes* to one colony in two separate instances. It should be noted that the 70% isopropyl alcohol vehicle had little anti-bacterial properties. The water was sterile and the alcohol tested negative in vitro. Therefore, they did not contribute other than as a vehicle for topical application in this environment.

The interval of 20 minutes was chosen for testing was similar to what would be expected if used as a surgical preparation.

The first and 2nd method of harvesting differed. The 2nd was accomplished with pressure wiping with the back end of a sterile scalpel so as to maximize the harvest even from sub surface sweat gland and hair follicles.

The strengths of this study were in the careful attention given to the method to disadvantage the topical applications effectiveness, yet PCA was effective and comparable to Betadine tested similarly as Phase 1. The PCA used was a single molecule of 99% pure biochemically synthesized PCA. The water an and the isopropyl alcohol could be discounted as a contributor to the effect as it contributed nothing to the bactericidal effect; sterile water and null effect of IPA in vitro testing.

The method used placed a burden on effectiveness of the reagents by the short time (20 minutes) to act and the 2nd harvest maximizing the potential yield due to the pressure scraping with back edge of a scalpel.

This study showed the effectiveness of a single reagent, PCA, the common phytochemical metabolite. It showed that a single concentrated metabolite working alone is bactericidal on human skin. It showed the importance of dose variation depending upon the intended topical application; wound versus intact skin. It showed the effectiveness absent any potential antibacterial boost from the isopropyl alcohol vehicle.

It established the criteria necessary for consideration as a drug; single reagent, known dose effective in two different host environments, topical application route, frequency of application (once), duration (20 min) time to gain the intended result.

Phase 3: Another test was conducted where the PCA was dissolved in 15 ml propylene glycol. The PPH is a skin penetration enhancer and assists in dissolving PCA.

In another test, 5 ml of essential oil of Peppermint was added. This has skin penetration enhancer properties and anti-microbial properties.

Based upon Phase I and II results, it was determined that the dose or concentration of PCA should be increased. It also was determined that it would be ideal to have something in the composition that possessed skin penetration properties. Therefore propylene glycol (PPG) was added. Fasano W J, ten Berge W F, Banton M I, Heneweer M, Moore N P. Dermal penetration of propylene glycols: measured absorption across human abdominal skin in vitro and comparison with a QSAR model. Toxicol In Vitro. 2011 December; 25(8):1664-70. Then to further the skin penetration an essential oil was added; i.e. an essence of peppermint oil (EOPO) (Nature oil, 1800 Miller Parkway, Streetsburo, Ohio 44241 100% pure [Japan]. Chen J, Jiang Q-D, Wu Y-M, Liu P, Yao J-H, Lu Q, Zhang H, Duan J-A. Potential of Essential Oils as Penetration Enhancers for Transdermal Administration of Ibuprofen to Treat Dysmenorrhoea Molecules 2015, 20, 18219-18236. Note that both PPG and EOPO are skin penetration enhancers but also have anti-microbial properties. *P. acnes* normally reside deep in the skin's hair follicles and or sebaceous glands. Therefore non-penetration common commercial disinfectants are not effective as reported in the literature and noted in the Background section above.

The composition of matter was created when 20 grams of PCA was placed in 85 ml 70% isopropyl alcohol making a concentration of PCA 17% (+/−). Then 15 ml propylene glycol and 5 ml of essential oil of peppermint were added. All reagents had skin penetration properties. The opposite shoulder had only the control 70% isopropyl alcohol vehicle applied. The subjects volunteered they liked the peppermint smell. The following summary is the no growth culture results after treatment.

| Reagent | Aerobic | Anaerobic |
|---|---|---|
| 17% +/− PCA composition | 10/12 | 11/12 |
| 70% IPA alone | 10/12 | 8/12 |

The analysis of the 2 pre PCA treatment subjects that grew subsequent positive cultures were analyzed as follows:

PCA Pre Treatment Aerobic Species Analysis:

The index subject #18 aerobic growth was too numerous to count. There were 2 different species; *Staphylococcus epidermidis/hominis* and *Micrococcus luteus*. The Subject #18's post PCA treatment aerobic culture, #20 showed 2 colonies; *S. capitis* and *S. epidermidis*. For reasons unknown, neither of these species was identified in the index culture, and both are considered non pathogens. The pre-PCA treatment index culture on subject #37 had colonies too numerous to count (TNTC) with heavy growth. The colony species were reported as one; *Staphylococcus capitus*. The Subject #37's post PCA treatment aerobic culture #39, showed one (1) colony growth, but not the former *S. capitus*, but was identified *Staphylococcus epidermidis* as the residual. As in prior phases, the residual growth was most often a non pathogen on aerobic culture.

Anaerobic Species Analysis:

The 17% PCA composite solution resulted in 11 of 12 subject's subsequent cultures having no growth. Pre PCA treatment subject #18 had bacteria colonies too numerous to count (TNTC) on anaerobic culture. There were 4 separate colonies with the following species; *S. epidermidis* (n=3) and *Propionibacterium avidium*. After this PCA treatment there was no anaerobic growth. Subject #37 index anaerobic culture showed 79 colonies. There were 4 prominent colony species; *Staphylococcus epidermidis, Staphylococcus capitis/caprae, Staphylococcus capitis* and *Propionibacterium acnes*. The one post PCA culture that showed a bacterial colony culture was subject #37 with post PCA treatment anaerobic culture being #39. There were 2 two colonies of same species; *Staphylococcus epidermidis*. There were no *Propionibacterium acnes* colonies. Thus, the results of Phase 3 showed the effectiveness of 17%+/−PCA in a composition of matter that had skin penetration properties; propylene glycol and essence of peppermint oil.

In Phase IV the method was different from the previous phases:

Method:

The variations in materials and methods in this phase were based upon results of the previous phases. They included changes in the solution, the method of dissolving the PCA, the timing of skin application, plus using two applications to simulate the present day recommendations of surgical skin preparation.

The solution used was 20 mg of ground PCA (Nanjing Zelang Medical Technology Co. Ltd.) in 95 ml 91% isopropyl alcohol and 5 ml of essential oil of peppermint 100% pure. The method placed the 20 grams of ground PCA in sterile container with volume markers. Then added 85 ml of 91% isopropyl alcohol; warm and shake. 5 ml of essential oil of peppermint was added. A repeat of warming and shaking was instituted. The container was filled to 100 ml, warm and repeated the shaking. It took perhaps 15 to 20 minutes for the ground crystals to dissolve.

An area was marked at 4 corners on the anterior axilla area of both shoulders. There was a topical reagent application. After 5 minutes a second application was made. The control group was again Chloroprep®. The experimental side was applied with manual motion and pressure on a sterile sponge soaked with the PCA solution. The subjects put hands on head for 10 minutes and then 10 minutes of moving arms around. Culture #1 was harvested with scraping at 20 minutes post $2^{nd}$ application. Subjects rested their arms at side for 40 minutes which is 60 minutes after the first application and 40 minutes after culture #1. A second culture is taken with scraping. The post application cultures were taken of each shoulder skin area with scraping with back side of a sterile surgical knife blade to maximize the yield.

Results of Phase IV:

The index pre-treatment culture's average colony counts of the 4 groups were similar.

|  | Aerobic | Anaerobic |
|---|---|---|
| PCA | 34.4 average | 44.4 average |
| Chloroprep ® | 41.75 average | 49.83 average |

The only group showing no growth in all 12 treated subjects was the PCA/peppermint solution treated aerobic group at 20 minutes. Other than that group, neither PCA nor Chloroprep® sterilized the skin 100% at 20 or 60 minutes. However, Chloroprep® had more "no growth" cultures in total. The following summary is the no growth cultures results after treatment.

|  | Aerobic | anaerobic |
|---|---|---|
| PCA 20 minutes | 12/12 | 4/12 |
| PCA 60 minutes | 7/12 | 6/12 |
| Chloroprep ® 20 minutes | 10/12 | 8/12 |
| Chloroprep ® 60 minutes | 10/12 | 10/12 |

The 20% PCA in 91% IPA and PPO was most effective at 20 minutes on aerobic culture, but not otherwise. Chloroprep® was partially effective at 20 minutes and maintained similar effectiveness on aerobic culture and same effectiveness on anaerobic cultures at 60 minutes. The results were different on Chloroprep at 20 minutes from Phase 1 when there was no growth following this reagent application.

There were 9 cultures that warranted selection for species determination. #8 pre PCA treatment anaerobic culture had 8 colony count but zero at 20 and 60 minutes. The interest was to learn what bacterial were eliminated. There were two species; *S. capitis* and *S. epidermidis*. #12 post PCA at 60 minutes showed 1 spreader colony on the plate (SPR) 50 colonies. This contrasted with the pre-treatment of 28 colonies. The species found in #12 aerobic were *Klebsiella pneumonia/oxytoca* and *Micrococcus leuteus*. These are not common pathogens. #14 pre PCA anaerobic showed 115 colonies. The species were *Propionbacterium acnes, S. ludgunessis* and *Kocuia varians*. There was no growth at 20 minutes showing that potential pathogen *P. acnes* was eliminated. However there were 4 aerobic colonies at 60 minutes in #19. They were: Gram Negative Rods: *Stenotrophomonas maltophilia*: rare pathogen and *Stenotrophomonas maltophilia*. The Gram Positive cocci were *Kytococcus sedentarius*: rare opportunistic pathogen and *Micrococcus luteus/lylae*: opportunistic pathogen, particularly in hosts with compromised immune systems, such as HIV patients. #19 was a pre PCA anaerobic culture with 39 count showing species of *P. acnes* and *S. epidermidis*. #21 was the post PCA at 20 minutes and showed 1 anaerobic colony of *P. acnes*, a reduction from 39 colonies.

There was culture of Gram Positive Rods with spores identified as: *Lysinibacillus sphaericus/fusiformis*: rare pathogen. #23 showed no growth at 60 minutes for aerobic or anaerobic. Therefore all aerobic bacteria including the one anaerobic colony of *P. acnes* was gone at 60 minutes. #31 aerobic was pre PCA showing 134 colonies. The species were *Micrococcus luteus* and *Micrococcus luteus/lylae*. There was no growth at 20 or 60 minutes of these normal flora species. #31 anaerobic was a pre PCA showing 28 colonies of *Staphylococcus ludgunensis* and *Bacillus cereus/thuringiensis*. There was no growth of either at 20 and 60 minutes. #32 was pre Chloroprep with aerobic colony count of 59 with the following species: *Micrococcus luteus/lylae*, *Micrococcus luteus* and *Kocuria Kristinae*. There was no colony growth at 20 or 60 minutes. #32 was pre Chloroprep anaerobic with 17 colonies with the following species: *S. epidermidis* and *Gemella Bergeri/sanguinis*. The post treatment showed no growth at 20 or 60 minutes. It should be noted in any of the literature or these experiments that re-colonization occurs with skin bacteria, likely in 30 minutes after treatment.

Species Analysis:

The pre-treatment species were predominately saprotrophic or commensal organisms. *Propionibacterium acnes* was identified in two subjects. After PCA treatment the specific species analysis showed predominately saprotrophic or commensal organisms. The potential pathogen *Propionibacterium acnes* was identified with 19 colonies pre-PCA treatment in #14 but showed no growth at 20 minutes after PCA treatment. *P. acnes* was identified pre-PCA treatment in #19 with 19 colonies and post treatment at 20 minutes there was one remaining colony of *P. acnes*. However there was no growth at 60 minutes.

Discussion of Phase IV:

This solution of 20 grams of PCA, 75 ml of 91% isopropyl alcohol and 5 ml of essence of peppermint oil was effective in removing potential pathogens, including *Propionibacaterium acnes*. Only commensal bacteria with rare pathogenicity remained. The control Cloroprep® did not removed most of the bacterial colonies, but not all. Many saprotrophic or commensal organisms were left intact. The PCA composition was not as effective as Cloroprep® against anaerobes, but where there was post PCA growth the species specific analysis showed that *Propionibacterium* was controlled.

A composite of the results based only no growth cultures following treatment by each solution are shown in FIG. 42. *Note that the 1% PCA was not included. The summation percentages of "no growth" are shown in FIG. 43.

Summary of the 4 Phase Testing at Loma Linda:

The questions proposed in the purpose of this proof of principle pilot study were answered in the affirmative. The optimal dose of PCA to act as a human skin disinfectant is greater than 10%. There is a facilitating delivery vehicle which is at least 70% isopropyl alcohol which allows higher concentrations of PCA to go into solution than water, propylene glycol and or essential oils alone. The results were optimized by the addition of known skin penetration enhancers; propylene glycol and essence of peppermint oil. *P. acnes* normally resides deep in the skin's hair follicles and or sebaceous glands. Therefore non-penetration common commercial disinfectants are not effective.

PCA in one or more of these vehicles provided a broad spectrum disinfectant effect comparable to existing commercial products; isopropyl alcohol, Chloroprep® and Betadine®.

One of two result assessment approaches was considered in this study. One is related to government regulations and is called non-inferiority status, or the showing the test article is essentially the same as a marketed product. The reason to choose this method is that the existing marketed products in the study had side effects, complications, and or higher cost. D'Agostino Sr R B, Massarol J M, Sullivan L M. Non-inferiority trials: design concepts and issues—the encounters of academic consultants in statistics Statist. Med. 2003; 22:169-186.

The other method is to establish clear superiority to an existing product. Both were considered in this study. The various PCA solutions showed a non-inferiority status to 70% Isopropyl alcohol, Betadine® and Chloroprep®. The PCA solutions in this study showed superiority to all but Chloroprep®. After the first Phase and each subsequent Phase results, the materials and methods were modified in attempt to improve the results of the test reagent PCA. The vehicle was changed from water to isopropyl alcohol to facilitate an increase dose of PCA. In addition, the vehicle was change to include reagents known to have skin penetration properties as well as antibiotic properties; i.e. propylene glycol and essence of peppermint oil. In Phase III the best PCA results in both aerobic and anaerobic cultures were obtained with a mixture of 17% PCA, propylene glycol and essence of peppermint oil. The anaerobic cultured bacteria are those likely to be below the skin surface and perhaps were affected by the addition of the skin penetrator enhancing reagents. PCA effectiveness was demonstrated in Phase I, even with the low dose of a 1.24% aqueous solution. This aqueous solution of PCA decreased the colonies of *Propionibacterium acnes* that were too numerous to count down to about to 1 and 5 colonies on same subject after treatment. Solutions of PCA at 10% or higher removed all pathogens, including *P. acnes*, but not all bacteria. Based upon the literature and the results of this study, the goal of complete sterilization of the human skin may not be possible, predictable or desirable. In fact, sterilization may not be desirable as it may eliminate bacteria that are beneficial to skin health and homeostasis. It does seem reasonable to remove all bacteria species that have pathologic potential. The irony of this goal is that it is reported that *Propionibacterium acnes* although in some instances has become a pathogen, it also has beneficial properties secreting a novel antioxidant. PCA which decreased and or eliminated *P. acnes* in these studies is an anti-oxidant so its presence as such may substitute for the biological anti-oxidant benefit of *P. acnes*. To further confuse any such study of this nature, it has been reported that the amount of bacteria on the skin prior to surgery are not directly related to surgical site infection. (Cronquist A B, Jokob K, Lai L, Latta P D, Larson E L. Relationship between Skin Microbial Counts and Surgical Site Infection after Neurosurgery. Clin Infect Dis. (2001) 33 (8):1302-1308).

In Phase I, Chloroprep® showed sterilization of the skin in all subjects. However this was not replicated in Phase IV at 20 minutes or at the extended time of 60 minutes. It should be noted that Saltzman, et al reported in the literature that Chloroprep® had a 7% incidence of residual bacteria; *Propionibacterium acnes* and *Staphylococcus aureus* persisted after treatment and his harvest was at a short time in which the reagent was still moist and there was not enough time perhaps for recolonization. (Saltzman M D, Nuber G W, Gryzlo S M, Mareck G S, Koh J L. Efficacy of Surgical Preparation Solutions in Shoulder Surgery. J Bone Joint Surg Am, 2009 Aug. 1; 91 (8): 1949-1953). There is no clear reason for the difference in Chloroprep® results in the literature since there were many variables in methods and timing of harvesting. There is not an apparent explanation for the differing results at 20 minutes in Phase I and IV in our study. Yet in Phase IV Chloroprep® was better than 20% PCA in 91% isopropyl alcohol and 5 ml of essence of peppermint oil except at 20 minute aerobic cultures, which were sterile with the PCA solution. Note that isopropyl alcohol was not in Phase IV solution.

Another measure of a treatment method would be the effectiveness to reduce bacteria colony counts. This was common with PCA solutions in all phases. A reduction in bacteria is a well-known principle in surgery in order to reduce the chance of infection. (Anglen J. Perspectives on Modern Orthopedics. Wound Irrigation in Musculoskeletal Injury. J Am Acad Ortho Surg. July/August 2001. 9 (4). 219-226).

The invention claimed is:

1. A bandage or wound dressing comprising protocatechuic acid impregnated on the bandage or wound dressing, wherein the protocatechuic acid has a purity of greater than 90%.

2. The bandage or wound dressing according to claim 1, wherein the protocatechuic acid is part of a solution.

3. The bandage or wound dressing according to claim 2, wherein the bandage or wound dressing has been sprayed or soaked with the solution, and wherein the protocatechuic acid becomes activated by contact with moisture from a wound.

4. The bandage or wound dressing according to claim 1, wherein the protocatechuic acid is a solid.

5. The bandage or wound dressing according to claim 1, wherein the bandage or wound dressing is made of a material selected from the group consisting of a cloth material, linen, metal, and sintered metallic mesh.

6. The bandage or wound dressing according to claim 1 in the form of a patch.

7. The bandage or wound dressing according to claim 1, wherein the protocatechuic acid is provided as part of a solution in an effective concentration of about 1% to about 50%, which elicits an effect selected from the group consisting of inhibiting microorganism growth and inhibiting microorganism survival.

8. The bandage or wound dressing according to claim 2, wherein the protocatechuic acid is present in the solution in a concentration of at least 25 mM.

9. The bandage or wound dressing according to claim 2, wherein the protocatechuic acid is about 1% to about 50% by weight (w/v) of the solution.

10. The bandage or wound dressing according to claim 2, wherein the solution further comprises a carrier that is selected from the group consisting of water, isopropyl alcohol, ethanol, propylene glycol, polyethylene glycol, or glycerol and mixtures or combinations thereof.

11. The bandage or wound dressing according to claim 2, wherein the solution further comprises an essential oil.

12. The bandage or wound dressing according to claim 2 wherein the solution further comprises isopropyl alcohol, propylene glycol, and an essential oil.

13. The bandage or wound dressing according to claim 10, wherein the isopropyl alcohol is present as a solution comprising about 70% to about 91% isopropyl alcohol.

14. The bandage or wound dressing according to claim 7, wherein the microorganism is selected from the group consisting of *C. difficile* 9689, *P. acnes* 6919, *C. Prefringens* 13124, *L. casei*, *E. coli* 8739, *E. coli* 43895, *S. Aureus* 6538, *S. Aureus* 33591, *S. mutans*, *S. pyogenes*, *P. aeruginosa* 9027, *K. pneumonia*, MRSE 51625, *C. albicans*, and *legionella* 43662.

15. The bandage or wound dressing according to claim 7, wherein the microorganism is part of a colony forming a biofilm.

16. A method of making a bandage or wound dressing impregnated with protocatechuic acid having a purity of greater than 90% comprising:
 a) providing a bandage or wound dressing material;
 b) impregnating the bandage or wound dressing material with the protocatechuic acid; and optionally
 c) drying the impregnated bandage or wound dressing material.

17. The method of claim 16, wherein the bandage or wound dressing material is impregnated by soaking or spraying the bandage or wound dressing material with a solution comprising an alcohol selected from isopropyl alcohol and ethyl alcohol, and wherein the solution further comprises the protocatechuic acid, and wherein the protocatechuic acid becomes activated by contact with moisture from a wound.

18. The method of claim 16, wherein the bandage or wound dressing material is impregnated with a solid form of the protocatechuic acid.

19. A method for treating a patient having a wound comprising applying a bandage or wound dressing to the wound, wherein the bandage or wound dressing has been impregnated or will subsequently be impregnated with protocatechuic acid having a purity of greater than 90% to a patient in need thereof, wherein the protocatechuic acid elicits an effect selected from the group consisting of inhibiting microorganism growth, and inhibiting microorganism survival, thereby treating the wound.

20. The method of claim 19, wherein the bandage or wound dressing is first applied to the wound and the wound dressing is then soaked or sprayed with a solution comprising the protocatechuic acid.

21. The method of claim 19, wherein the microorganism is selected from *C. difficile* 9689, *P. acnes* 6919, *C. Prefringens* 13124, *L. casei*, *E. coli* 8739, *E. coli* 43895, *S. Aureus* 6538, *S. Aureus* 33591, *S. mutans*, *S. pyogenes*, *P. aeruginosa* 9027, *K. pneumonia*, MRSE 51625, *C. albicans*, and *legionella* 43662.

22. The method of claim 19, wherein the wound is a burn, skin break, bone break, muscle tear, puncture, surgical incision site, microdermabrasion site, skin graft site, a wound associated with diabetes, a bed sore, a pressure sore, skin defoliation, or a laceration, and wherein the protocatechuic acid becomes activated by contact with moisture from the wound.

* * * * *